United States Patent [19]
Baker et al.

[11] Patent Number: 5,668,127
[45] Date of Patent: Sep. 16, 1997

[54] NITROIMIDAZOLE ANTIBACTERIAL COMPOUNDS AND METHODS OF USE THEREOF

[75] Inventors: William R. Baker, Bellevue; Cai Shaopei; Eric L. Keeler, both of Seattle, all of Wash.

[73] Assignee: PathoGenesis Corporation, Seattle, Wash.

[21] Appl. No.: 496,850

[22] Filed: Jun. 26, 1995

[51] Int. Cl.$^6$ ............ C07D 265/12; C07D 267/12; C07D 267/22
[52] U.S. Cl. ............ 514/183; 514/211; 514/230.5; 540/468; 540/552; 544/91
[58] Field of Search ............ 544/91; 514/230.5, 514/183, 211; 540/468, 552

[56] References Cited

U.S. PATENT DOCUMENTS

| | | |
|---|---|---|
| 3,978,211 | 8/1976 | Coronelli et al. |
| 5,317,019 | 5/1994 | Bender et al. .............. 514/224.2 |

OTHER PUBLICATIONS

Sehgal, R.K. and Agrawal, K.C., "Novel Nitroimidazo[2,1-b]oxazole Formation Reaction of 2,4(5)-Dinitroimidazole with Oxiranes (1)," *J. Heterocyclic Chem.* 16:1499–1500 (1979).

Agrawal, K.C. et al., "Potential Radiosensitizing Agents. Dinitroimidazoles," *J. Chem.* 22(5):583–586 (1979).

Sehgal, R.K. et al, "Potential Radiosensitizing Agents. 2. Synthesis and Biologica Activity of Derivatives of Dinitroimidazole with Oxiranes," *J. Med. Chem.* 24:601–604 (1981).

Nagarajan, K. et al., "Nitroimidazoles XXI. 2,3-dihydro-6-nitroimidazo [2.1-b]oxazoles with antitubercular activity," *Eur. J. Med. Chem.* 24:631–633 (1989).

Ashtekar, D.R. et al, "In Vitro and In Vivo Activities of the Nitroimidazole CGI 17341 against *Mycobacterium tuberculosis*," *Antimicrob. Agents Chemother.*, 37(2):183–186 (1993).

Aronsson, B. et al., *J. Infect. Dis.* 151:476–481 (1985).

Dosik, G.M. et al., *Am. J. Med.* 67:646–656 (1979).

Bartlett, J., see *Clostridium difficle: Its role in Intestinal Disease*. R.D. Rolfe an S.M. Finegold, eds., Academic Press Inc., New York, 1988 pp. 1–13.

Swannson, B. et. al., *Antimicrob. Agents Chemother.*, 35:1108–1111 (1991).

Bartlett, J.G. et al., *Clin. Infect. Dis.* (S4) S265–72 (1994).

Physician's Desk Reference, 48th Edition, pp. 1704–1706 (1994).

*IUPAC 1974 Recommendations for Section E, Fundamental Stereochemistry, Pure Appl. Chem.*, 45:13–30 (1976).

Chemical Abstracts Index Guide–Appendix IV, paragraph 203 (1987).

Bundle, D.R. et al., *J. Chem. Soc.*, Perkin Trans. I, 11:2247–2250 (1985).

(List continued on next page.)

*Primary Examiner*—Mukund J. Shah
*Assistant Examiner*—Tamthom T. Ngo
*Attorney, Agent, or Firm*—Christensen O'Connor Johnson & Kindness PLLC

[57] ABSTRACT

Methods, compounds and compositions are provided for inhibiting the growth of pathogenic mycobacteria in vitro and of treatment of pathogenic bacterial infections, such as mycobacterial and clostridium infections, in vivo using bicyclic nitroimidazole compounds of the formula (II):

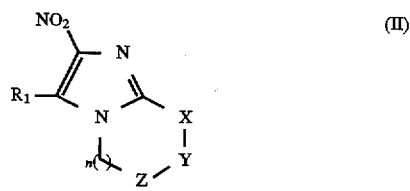

wherein $R_1$ is hydrogen, halogen, loweralkyl, haloloweralkyl, cycloalkyl, heterocycle, substituted heterocycle and heterocyclicalkyl; X is oxygen, sulfur or $NK_2$, where $R_2$ is hydrogen, loweralkyl, aryl, cycloalkyl, heterocycle, substituted heterocycle, heterocyclicalkyl, $COR_3$ or $SO_2R_4CONR_4R_5$, where $R_4$ and $R_5$ are independently selected from hydrogen, loweralkyl, aryl, alkylaryl, alkoxyalkyl, alkoxyaryl, alkoxyalkoxyaryl, alkylheterocycle, and alkoxyheterocycle; n is 1, 2 or 3; Y and Z are independently selected $CH_2$, CO, $CR_4R_5$ or $NR_4$, where $R_4$ and $R_5$ are as defined above; provided that when n is 2 or 3, the compounds of formula II can be additionally substituted as follows:

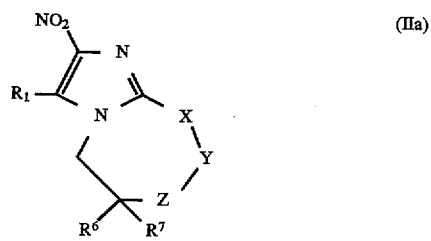

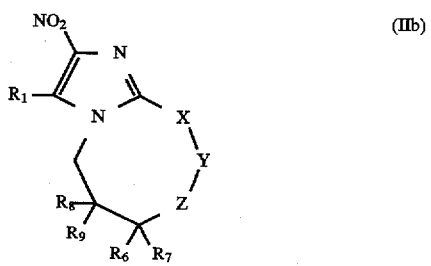

wherein $R_6$, $R_7$, $R_8$ and $R_9$ are independently selected from hydrogen, loweralkyl, aryl, alkylaryl, alkoxyalkyl, alkoxyaryl, alkoxyalkoxyaryl, alkylheterocycle, and alkoxyheterocycle; and the pharmaceutically acceptable salts thereof. The methods, compounds and compositons are particularly useful for inhibiting the growth of *Mycobacterium tuberculosis* and *Clostridium difficile*.

15 Claims, 5 Drawing Sheets

OTHER PUBLICATIONS

Liu, H. et al., *J. Org. Chem.*, 57:2471 (1992).

Pandey, G.D. et al., *Pol. J. Chem.*, 54:763 (1980).

Spangler, S.K. et al. "Oxyrase, a method which avoids $CO_2$ in the incubation atmosphere for anaerobic susceptibility testing of antibiotics affected by $CO_2$," *J. Microbiol.* 31:460–462 (1993).

Spangler, S.K. et al., "Susceptibilities of 201 anaerobes to erythromycin, azithromycin, clarithromycin, and roxithromycin by Oxyrase agar dilution and E-t methodologies," *J. Clin. Microbiol.* 33:1366–1367 (1995).

Barry, A.L. et al., "In-vitro potency of azithromycin against gram-negative bacilli method-dependent," *J. Antimicrob. Chemother.* 28: 607–610 (1991).

Hansen, S.L. et al., "Effect of carbon dioxide and pH on susceptibility of *Bactero fragilis* group to erythromycin," *Antimicrob. Agents Chemother.*, 19: 335–336 (1990).

Retsema, J.A. et al., "Significance of environmental factors on the in vitro potenc azithromycin," *Eur. J. Clin. Microbiol. Infect. Dis.* 10:834–842 (1991).

Bartlett, J.G., "*Clostridium difficile:* History of Its Role as an Enteric Pathogen the Current State of Knowledge About the Organism," *Clin. Infect. Dis.*, 18(Suppl. 4):S265–S272 (1994).

Ahmad, S.H. et at., "Antibiotic Associated Colitis," *Indian J. Pediatri.*, 60:591–5 (1993).

Anand, A., et al., "Epidemiology, Clinical Manifestations, and Outcome of *Clostridium difficile*–Associated Diarrhea," *Am. J. Gastro.*, 89(4):519–523 (1994).

Mitty, Roger D. and Lamont, J.T., "*Clostridium difficile* Colitis: Epidemiology, Pathophysiology, and Treatment," *Mt. Sinai J. Med.*, 61(4):329–335 (1994).

Samore, M.H. et al., "*Clostridium difficile* Colonization and Diarrhea at a Tertiar Care Hospital," *Clin. Infect. Dis.*, 18:181–187 (1994).

Fekety, R., "Antibiotic–Associated Colitis," In: Mandell G.L., ed., *Principles and Practice of Infectious Diseases*, Part II, Major Clinical Syndromes, Ch. 78, pp. 978–987. (1995).

Fekety, R. and Shah., A.B., "Diagnosis and Treatment of *Clostridium difficile* Colitis," *JAMA*, 269(1):71–75 (1993).

Gorbach, S.L., "*Clostridium difficile* Settles In a Nursing Home," *Hospital Practice*, pp. 145–160 (Feb. 15, 1989).

Kofman, T.P. et al., "α–Oxides in Reactions with NH Acids of the Heterocyclic Series. II. Alkylation of 3,5–Dinitro–1,2,4–Triazole with Olefin Oxides," (translat from *Khimiya Geterotsiklicheskih Soedinenii*, 5:705–707 (1975)), Plenum Publishing Corporation, pp. 612–614 (1976).

Nagarajan, K. et at., "Nitroimidazoles: Part XIX—Structure–activity Relationship" *Indian J. Chem.*, 23:342–362 (1984).

Nagarajan, K. and Shenoy, S.J., "Nitroimidazoles: Part XX—Reactions of 2,4–Dinitroimidazole with 2–Haloethanols, 3–Chloropropionitrile & Propylene Oxide", *Indian J. Chem.*, 23:363–368 (1984).

B = absent, C(R_6R_7) or C(R_8R_9)C(R_6R_7)

NITROIMIDAZOLE ANTIBACTERIAL COMPOUNDS AND METHODS OF USE THEREOF

FIELD OF THE INVENTION

The present invention relates to new nitroimidazole derivatives which are useful in killing bacteria, such as mycobacteria and clostridium, to antimicrobial compositions containing the compounds and to the use of the compounds and compositions, alone or in combination with other antimicrobial agents, in the treatment of pathogenic infections, such as mycobacterial and clostrium infections.

BACKGROUND OF THE INVENTION

After a decline in rates of infection over several decades, a disturbing increase in the incidence of tuberculosis (TB) is occurring. Because TB is highly contagious it poses a profound threat to public health. TB bacteria are easily passed from person to person in airborne droplets formed when a person with active TB sneezes or coughs.

Even more alarming has been the rise of multidrug-resistant tuberculosis (MDRTB). Prior to 1984, about 10% of TB bacteria isolated from patients in the United States were resistant to even a single antibacterial drug. In 1984, 52% of patients were infected with *Mycobacterium tuberculosis* (also referred to as tubercle bacilli) resistant to at least one drug, and 32% were resistant to one or more drugs. Outbreaks of MDRTB have been reported in 13 states. Ten percent of the recorded MDRTB cases to date have occurred in previously healthy people whose mortality rate—70 to 90%—has been nearly the same as that of immunosuppressed persons with MDRTB (Snider and Roper, 1992).

The United States Centers for Disease Control (CDC) has released preliminary results of a joint study with the New York State Health Department showing that cases of drug-resistant TB have more than doubled since 1984. CDC data from the first quarter of 1991 show that many of these drug-resistant strains are resistant to both of the frontline TB drugs, rifampin and isoniazid. Outbreaks of MDRTB have occurred in hospitals in Miami and New York City, as well as in the New York State prison system. In one hospital in New York City, the median interval between diagnosis of MDRTB and death was only four weeks. Additional clusters of MDRTB were reported to the CDC in 1990 and 1991 from Mississippi, Missouri, and Michigan.

There are five frontline drugs known to be highly effective against *Mycobacterium tuberculosis* and five second-line drugs that can be used when resistance to one or more of the frontline drugs is detected. Ironically, in the United States, until April 1992, there were shortages of antituberculosis drugs, some of which are crucially needed when resistance to the frontline drugs rifampin and isoniazid is present. These shortages had occurred because several pharmaceutical companies had ceased production of these drugs.

Because of its persistence in the body, the tubercle bacillus is a notoriously difficult pathogen to control. Although bacille Calmette-Guerin (BCG) vaccine protects against severe tuberculosis meningitis and disseminated TB in children, its efficacy against pulmonary TB in adults has varied widely in different parts of the world. Treatment of conventional TB is effective, but expensive, requiring daily treatment with multiple drugs for a minimum of six months. There is a common tendency among TB patients to stop taking their drugs when the drugs begin to have their beneficial effect or to take the medications only intermittently. When this happens, relapses are frequent and very often are caused by drug-resistant tubercle bacilli that have survived the initial course of treatment. The emergence of drug-resistant *M. tuberculosis* is in many ways an index of individual compliance with antituberculosis chemotherapy and of the inability of the health care infrastructure to ensure adequate treatment. Many public health agencies that once could play key roles in this process have had their budgets cut drastically in recent years and hence are unable to perform this crucial service.

MDRTB is extraordinarily difficult to treat, and a majority of patients do not respond to therapy. Total treatment costs for an individual with MDRTB can be as much as ten times the cost of traditional treatment; the cost of the treatment drugs alone can be as much as 21 times as great.

The preferred treatment for classical TB consists of isoniazid, rifampin, and pyrazinamide. For patients whose tubercle bacilli are thought to be resistant to isoniazid, a fourth drug, ethambutol, is commonly added to the regimen until drug susceptibility results are known. Isolates of tubercle bacilli resistant to both isoniazid and rifampin, now representing about 20% in some cities, require specialized treatment with additional medications, which may include streptomycin and ciprofloxacin for almost two years.

The tubercle bacillus is a slow-growing organism. Three to six weeks are needed to grow the bacteria in the clinical laboratory, and an additional three to six weeks are needed to screen for antibiotic resistance. Such extended laboratory procedures can result in a delay in diagnosis, which means that patients with unrecognized drug-resistant TB may be treated ineffectively and remain infectious for a longer period. In HIV-positive individuals, MDRTB usually causes death within 4 to 16 weeks after being diagnosed, which is often before laboratory tests on drug susceptibility and resistance can be completed.

There is no evidence that mutation rates in *M. tuberculosis* organisms have increased or that increased virulence is to blame for the recent deadly outbreaks of TB. It is likely that drug-resistant forms of tuberculosis arose because of patient noncompliance with the 6- to 12-month regimen of antibiotics required to treat TB. Ineffective treatment regimens also play a role in the rising incidence of TB. To address noncompliance, some states with high TB rates are considering approaches to outreach, such as expanding directly observed therapy (DOT); others may reestablish inpatient facilities similar to the TB sanatoria of the first half of this century. Standard treatment regimens for TB have also been updated. Instead of taking two or three antibiotics, TB patients now take four. Still, as noted earlier, the current shortages of antituberculosis drugs in the United States have made even standard treatment difficult.

A series of nitroimidazo[2,1-b]oxazole dedvates was described in Sehgal, K. et al., "Novel Nitroimidazo[2,1-b] oxazole Formation from Reaction of 2,4(5)-Dinitroimidazole with Oxiranes (1)," *J. Heterocyuclic Chem.* 16:1499–1500 (1979). Compounds of this type have the following general formula (I):

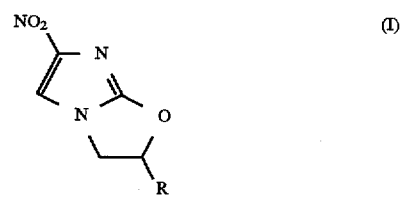

These compounds were described as potential radiosensitizing agents for use in the radiotherapy of cancer (Agrawal, K.

et al., "Potential Radiosensitizing Agents. Dinitroimidazoles," *J. Med Chem.* 22(5):583–586 (1979); Sehgal, R. et al, "Potential Radiosensitizing Agents. 2. Synthesis and Biological Activity of Derivatives of Dinitroirnidazole with Oxiranes,"*J. Med. Chem.* 24:601–604 (1981). More recently, certain nitroimidazole compounds were reported to exhibit antimicrobial properties, including antitubercular activity (see, e.g., Nagarajan, K. et al., "Nitroimidazoles XXI. 2,3-dihydro-6-nitroimidazo [2, 1-b] oxazoles with antitubercular activity," *Eur. J. Med Chem.* 24:631–633 (1989). In addition, the compound of formula (I) in which R is ethyl (2-ethyl-5-nitro-2,3-dihydro[2,1-b] imidazo-oxazole, also known as Ceiby-Geigy CGI 17341) has recently been shown to exhibit activity against *Mycobacterium tuberculosis* (Ashtekar, D. et al, "In Vitro and In Vivo Activities of the Nitroimidazole CGI 17341 against *Mycobacterium tuberculosis*," *Antimicrobial Agents and Chemotherapy*, 37(2):183–186 (1993).

Pseudomembranous colitis (PMC) is a serious intestinal disease marked by severe colonic intimation, diarrhea, abdominal cramps, and mucosal plaques or pseudomembranes. PMC is caused by the over production of toxigenic *Clostridium difficile* in the gut. *C. difficile* is a spore-forming anaerobe and is the major nosocomial pathogen of PMC. The over growth of *C. difficile* occurs when the bacterial flora of the GI tract has been modified due to extensive use of broad spectrum antibiotics. Two toxins, A and B, are produced by *C. difficile*. The toxins attack membranes or microfilaments of colon cells producing inflamation and necrosis. Toxin A causes intestinal hemorrhage and fluid secretion while toxin B is cytotoxic.

PMC as a subclass of diarrheal disease has become a frequent complication of antibiotic use. PMC normally appears 5–10 days after onset of antibiotic therapy. A watery diarrhea is the most common symptom, occuring in 90–95% of all PMC cases (B. Aronsson et al. *J. Infect. Dis.* 151:476–481 (1985)). Sever cases of PMC can cause high fever, leukocytosis, dehydration, electrolyte imbalance, and death (see *Clostridium difficle*: Its role in Intestinal Disease. Ed. R. D. Kolfe and S. M. Finegold, Academic Press Inc., New York, 1988 and R. Fekety, ÒAntibiotic-Associated Colitis. Mediguide to Infectious DiseaseÓ Vol 4, pp 1–7, 1984).

Patients at greatest risk include the eldery, debilitated cancer patients, and patients undergoing abdominal surgery. Untreated *C. difficile* produces 10–20% mortality in elderly or chronically debilitated patients (G. M. Dosik et al., *Am. J. Med.* 67:646–656 (1979)). Worldwide incidence of PMC is unknown due to the lack of appropriate studies. However, in industrialized countries, *C. difficile* is rapidly becoming the most common enteric bacterial pathogen after Campylobacter and Salmonella (J. Bartlett, see *Clostridium difficle*: Its role in Intestinal Disease. Ed. R. D. Rolfe and S. M. Finegold, Academic Press Inc., New York, 1988 pp. 1–13).

Antibiotics most frequently used to treat PMC include vancomycin, metronidazole, and bacitracin. Vancomycin is a very expensive treatment, $100–400 for a ten day course. Relapse rate after vancomycin therapy has been shown in experimental animals (B. Swannson et. al, *Antimicrobial Agents and Chemotherapy*, 35:1108–1111 (1991) and J. G. Bartlett et al., *Clin. Infect. Dis.* (S4) S265–72 (1994)). Due to the increase of vancomycin resistant bacteria, the use of vancomycin for *C. difficile* infections may be on the decline. Metronidazole is less effective than vancomycin, however, its also less expensive. Metronidazole is orally absorbed and may expose patients to potential side effects that are associated with the drug (PHYSICIANS DESK REFERENCE, 48TH EDITION, 1994, pp- 1704–1706). Metronidazole has a relapse rate similar to vancomycin. Bacitracin is a antibiotic polypeptide and is commerically available as a mixture of nine peptides. It is also expensive and no convenient oral dosage form is available.

A need continues in the art, however, for improved agents that exhibit antimicrobial activity against pathogenic mycobacteria, and more particularly for agents and their derivatives that may be highly useful in the treatment of MDRTB.

SUMMARY OF THE INVENTION

It has now been surprisingly discovered that pathogenic mycobacteria can be controlled in vitro or in vivo by certain nitroimidazole derivatives. Accordingly, the present invention provides methods of inhibiting the growth of pathogenic mycobacteria in vitro and of treatment of pathogenic mycobacterial infections in vivo using dinitroimidazole compounds of the formula (II):

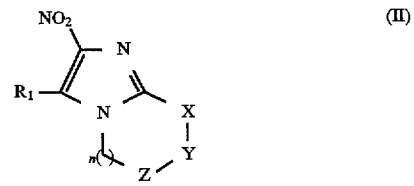

wherein $R_1$ is hydrogen, halogen, loweralkyl, haloloweralkyl, cycloalkyl, heterocycle, substituted heterocycle and heterocyclicalkyl;

X is oxygen, sulfur or $NR_2$, where $R_2$ is hydrogen, loweralkyl, aryl, cycloalkyl, heterocycle, substituted heterocycle, heterocyclicalkyl, $COR_3$ or $SO_2R_4CONR_4R_5$, where $R_3$, $R_4$ and $R_5$ are independently selected from hydrogen, loweralkyl, aryl, alkylaryl, alkoxyalkyl, alkoxyaryl, alkoxyalkoxyaryl, alkylheterocycle, and alkoxyheterocycle;

n is 1, 2 or 3;

Y and Z are independently selected from oxygen, $CH_2$, CO, $CR_4R_5$ or $NR_4$, where $R_4$ and $R_5$ are as defined above;

provided that when n is 2 or 3, the compounds of the invention can be additionally substituted as shown in the following formulas IIa and IIb, respectively:

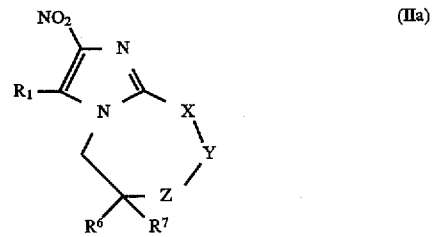

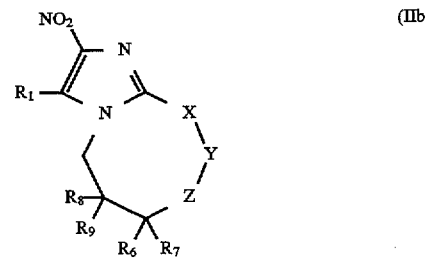

wherein $R_6$, $R_7$, $R_8$ and $R_9$ are independently selected from hydrogen, loweralkyl, aryl, alkylaryl, alkoxyalkyl, alkoxyalkylaryl, alkoxyalkylheterocycle, alkylarylalkylaryl, alkylarylaryl, alkylcycloalkyl, alkoxyaryl, alkylheterocycle, and alkoxyheterocycle;

and the pharmaceutically acceptable salts thereof.

Presently particularly preferred and novel compounds of the invention are provided by the compounds of formula (II) having a backbone structure wherein X is oxygen, according to formula (III):

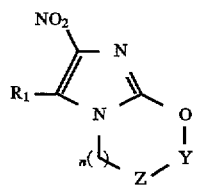
(III)

wherein $R_1$, Y, Z and n are as defined above, resulting in the following embodiments IIIa, IIIb and IIIc when n is 1, 2 or 3, respectively:

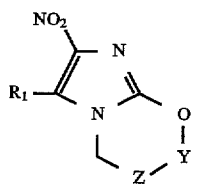
(IIIa)

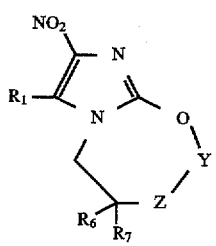
(IIIb)

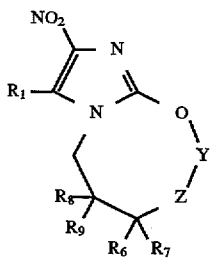
(IIIc)

wherein $R_6$, $R_7$, $R_8$ and $R_9$ are as defined above.

In a presently preferred embodiment for the treatment of tuberculosis, the methods and compounds of the invention may be employed alone, or in combination with other anti-*Mycobacterium tuberculosis* agents, such as isoniazid, rifampin, pyrazinamide, rifabutin, streptomycin and ciprofloxacin, to provide new agents for the treatment of tuberculosis, including MDRTB.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein.

In the accompanying drawings.

DETAILED DESCRIPTION OF THE PREFERRED EMBODIMENT

Figure 1:
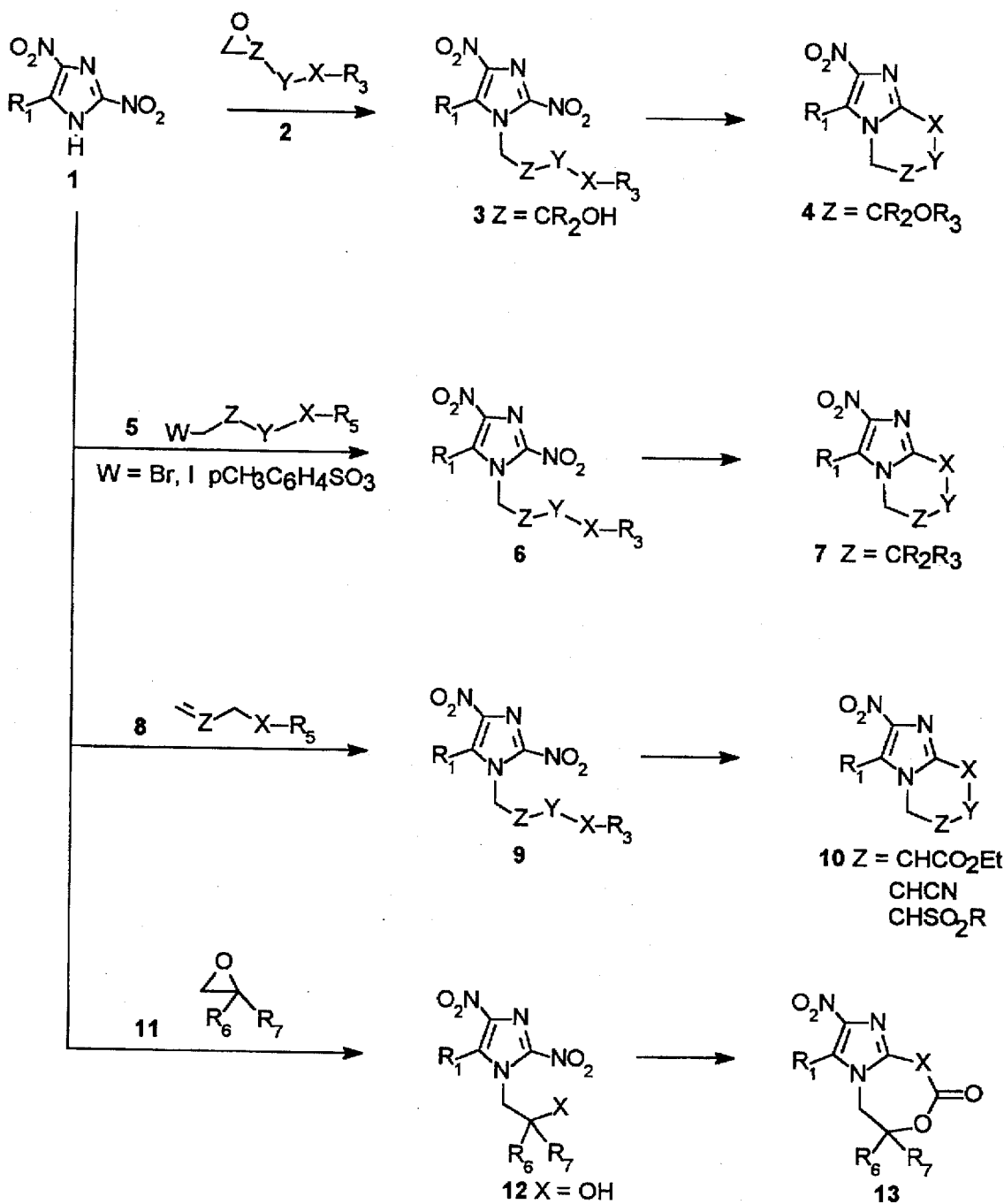
FIG. 1 is a schematic representation of alternative synthesis pathways of compounds of the invention.

In accordance with the present invention, methods are provided for control of pathogenic roycebacteria, either in vitro or in vive. Thus, in one aspect the present invention provides a method of inhibiting the growth of *Mycobacterium sp.* in vitro comprising contacting the *Mycobacterium sp.* with a growth inhibitory amount of a dinitroimidazole compounds of the formula (II):

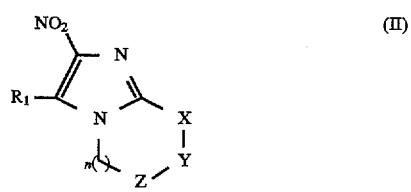
(II)

wherein $R_1$ is hydrogen, halogen, loweralkyl, halloloweralkyl, cycloalkyl, heterocycle, substituted heterocycle and heterocyclicalkyl;

X is oxygen, sulfur or $NR_2$, where $R_2$ is hydrogen, loweralkyl, aryl, cycloalkyl, heterocycle, substituted heterocycle, heterocyclicalkyl, $COR_3$ or $SO_2R_4CONR_4R_5$, where $R_3$, $R_4$ and $R_5$ are independently selected from hydrogen, loweralkyl, aryl, alkylaryl, alkoxyalkyl, alkoxyaryl, alkoxyalkoxyaryl, alkylheterocycle, and alkoxyheterocycle;

n is 1, 2 or 3;

Y and Z are independently selected from oxygen, $CH_2$, CO, $CR_4R_5$ or $NR_4$, where $R_4$, and $R_5$ are as defined above;

provided that when n is 2 or 3, the compounds of the invention can be additionally substituted as shown in the following formulas IIa and IIb, respectively:

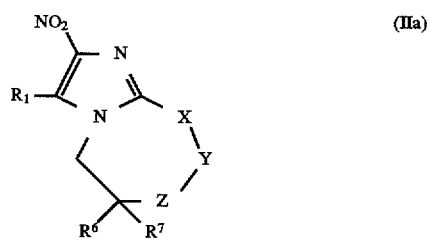
(IIa)

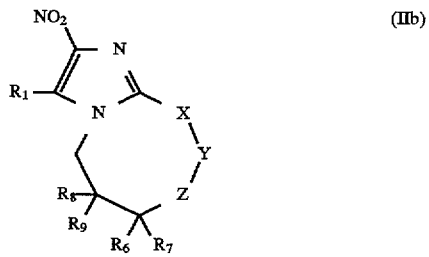
(IIb)

wherein $R_6$, $R_7$, $R_8$ and $R_9$ are independently selected from hydrogen, loweralkyl, aryl, alkylaryl, alkoxyalkylaryl, alkoxyalkylheterocycle, alkylarylalkylaryl, alkylarylaryl, alkylcycloalkyl, alkoxyalkyl, alkoxyaryl, alkylheterocycle, and alkoxyheterocycle;

and the pharmaceutically acceptable salts thereof.

In another aspect, the present invention provides methods of treating human or animal subjects suffering from a pathogenic mycobacterial infection, e.g., tuberculosis, whether of sensitive-strain or multi drug-resistant strain (MDRTB) origin. Thus, the present invention provides a method of treating a human or animal subject in need of such treatment comprising administering to the subject a therapeutically effective amount of a dinitroimidazole compound of formula (II), above, either alone or in combination with other antibacterial or antifungal agents.

In another aspect, the present invention provides new antimicrobial dinitroimidazole compounds of the formula (II):

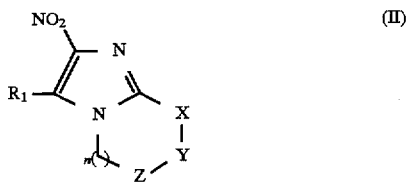

wherein $R_1$ is hydrogen, halogen, loweralkyl, haloloweralkyl, cycloalkyl, heterocycle, substituted heterocycle and heterocyclicalkyl;

X is oxygen, sulfur or $NR_2$, where $R_2$ is hydrogen, loweralkyl, aryl, cycloalkyl, heterocycle, substituted heterocycle, heterocyclicalkyl, $COR_3$ or $SO_2R_4CONR_4R_5$, where $R_3$, $R_4$ and $R_5$ are independently selected from hydrogen, loweralkyl, aryl, alkylaryl, alkoxyalkyl, alkoxyaryl, alkoxyalkoxyaryl, alkylheterocycle, and alkoxyheterocycle;

n is 1, 2 or 3;

Y and Z are independently selected from oxygen, $CH_2$, CO, $CR_4R_5$ or $NR_4$, where $R_4$ and $R_5$ are as defined above;

provided that when n is 2 or 3, the compounds of the invention can be additionally substituted as shown in the following formulas IIa and IIb, respectively:

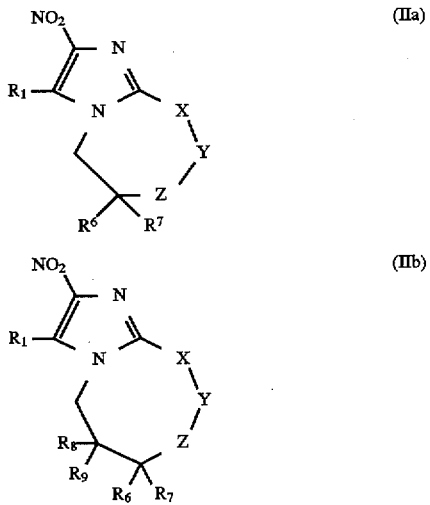

wherein $R_6$, $R_7$, $R_8$ and $R_9$ are independently selected from hydrogen, loweralkyl, aryl, alkylaryl, alkoxyalkylaryl, alkoxyalkylheterocycle, alkylarylalkylaryl, alkylarylaryl, alkylcycloalkyl, alkoxyalkyl, alkoxyaryl, alkylheterocycle, and alkoxyheterocycle;

and the pharmaceutically acceptable saks thereof.

As used above and elsewhere herein the following terms have the meanings defined below:

The term "pathogenic mycobacteria" refers to mycobacterial organisms which do not normally reside in a human or animal host, and which are capable of causing a disease state in the host. Representative examples of pathogenic mycobacteria include, for example, *Mycobacteria tuberculosis, Mycobacteria leprae, Mycobacteria avium* complex, and the like, including multidrug-resistant *M. tuberculosis* strains.

The term "acylamino" means an acyl (CO—) radical to which an amino group is appended.

The term "loweralkyl" as used herein refers to branched or straight chain alkyl groups comprising one to ten carbon atoms that are unsubstituted or substituted, e.g., with one or more halogen groups, including, e.g., methyl, ethyl, propyl, isopropyl, n-butyl, t-butyl, neopentyl, trifluoromethyl, pentafluoroethyl and the like.

The term "alkoxy" as used herein refers to RO— wherein R is loweralkyl as defined above. Representative examples of lower alkoxy groups include methoxy, ethoxy, t-butoxy, trifluoromethoxy and the like. The term "aryl" as used herein refers to a phenyl or a $C_9$— or $C_{10}$-bicyclic carbocyclic ring system having one or more aromatic rings, including naphthyl, tetrahydronaphthyl, indanyl, indenyl and the like. Aryl groups can be unsubstituted or substituted with one, two, three, four or five substituents independently selected from loweralkyl, haloalkyl, alkoxy, aryl, alkoxyaryl and halo.

The term "alkylaryl" as used herein refers to a loweralkyl radical to which is appended an aryl group. Representative arylalkyl groups include benzyl, phenylethyl, hydroxybenzyl, fluorobenzyl, fluorophenylethyl and the like.

The term "arylalkylaryl" as used herein refers to an alkylaryl group as previously defined appended to an aryl group. Representative alkylarylaryl groups include 4-benzylphenyl, 3-benzylphenyl, 4-phenethylphenyl and the like.

The term "arylaryl" as used herein refers to an aryl group as previously defined which is appended to an aryl group. Representative arylaryl groups include biphenyl, 4-(1-naphthyl)phenyl, 4-(2-naphthyl)phenyl and the like.

The term "aryloxy" as used herein refers to RO— wherein R is an aryl group. Representative arylalkoxy group include benzyloxy, phenylethoxy and the like.

The term "alkoxyaryl" as used herein refers to a lower alkoxy radical to which is appended an aryl group. Representative arylalkoxy group include benzyloxy, phenylethoxy and the like.

The term "cycloalkyl" as used herein refers to an alicyclic group comprising from 3 to 7 carbon atoms including, but not limited to, cyclopropyl, cyclobutyl, cyclopentyl, cyclohexyl and the like.

The term "alkylcycloalkyl" as used herein refers to a loweralkyl radical to which is appended a cycloalkyl group. Representative examples of alkylcycloalkyl include cyclopropylmethyl, cyclohexylmethyl, 2-(cyclopropyl)ethyl and the like.

The term "halogen" or "halo" as used herein refers to iodo, bromo, chloro or fluoro.

The term "haloalkyl" as used herein refers to a lower alkyl radical, as defined above, bearing at least one halogen substituent, for example, chloromethyl, fluoroethyl or trifluoromethyl and the like.

The term "heterocycle" as used herein refers to an aromatic ring system composed of 5 or 6 atoms selected from the heteroatoms nitrogen, oxygen, and sulfur. The heterocycle maybe composed of one or more heteroatoms that are either directly connected such as pyrazole or connected through carbon such as pyrimidine. Heterocycles can be substituted or unsubstituted with one, two or three substituents independently selected from amino, alkylamino, halogen, alkyl acylamino, toweralkyl, aryl, alkoxy.

The term "substituted heterocycle" or "heterocyclic group" or heterocycle as used herein refers to any 3- or 4-membered ring containing a heteroatom selected from nitrogen, oxygen, and sulfur or a 5- or 6-membered ring containing from one to three heteroatoms selected from the group consisting of nitrogen, oxygen, or sulfur; wherein the 5-membered ring has 0–2 double bounds and the 6-membered ring has 0–3 double bounds; wherein the nitrogen and sulfur atom maybe optionally oxidized; wherein the nitrogen and sulfur heteroatoms maybe optionally quarternized; and including any bicyclic group in which any of the above heterocyclic rings is fused to a benzene ring or another 5- or 6-membered heterocyclic ring independently defined above. Heterocyclics in which nitrogen is the heteroatom are preferred. Fully saturated heterocyclics are also preferred. Preferred heterocycles include: diazapinyl, pyrryl, pyrrolinyl, pyrrolidinyl, pyrazolyl, pyrazolinyl, pyrazolidinyl, imidazoyl, imidazolinyl, imidazolidinyl, pyridyl, piperidinyl, pyrazinyl, piperazinyl, N-methyl piperazinyl, azetidinyl, N-methylazetidinyl, pyrimidinyl, pyddazinyl, oxazolyl, oxazolidinyl, isoxazolyl, isoazolidinyl, morpholinyl, thiazolyl, thiazolidinyl, isothiazolyl, isothiazolidinyl, indolyl, quinolinyl, isoquinolinyl, benzimidazolyl, benzothiazolyl, benzoxazolyl, furyl, thienyl, triazolyl and benzothienyl.

Heterocyclics can be unsubstituted or monosubstituted or disubstituted with substituents independently selected from hydroxy, halo, oxo (C=O), alkylimino (RN=, wherein R is a loweralkyl group), amino, alkylamino, dialkylamino, acylaminoalkyl, alkoxy, thioalkoxy, polyalkoxy, loweralkyl, cycloalkyl or haloalkyl. The most preferred heterocyclics include imidazolyl, pyridyl, piperazinyl, azetidinyl, thiazolyl, triazolyl and the following:

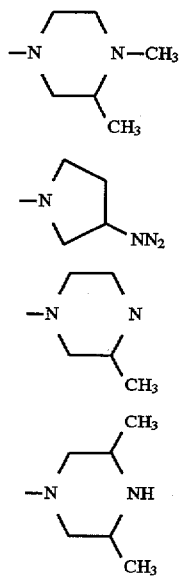

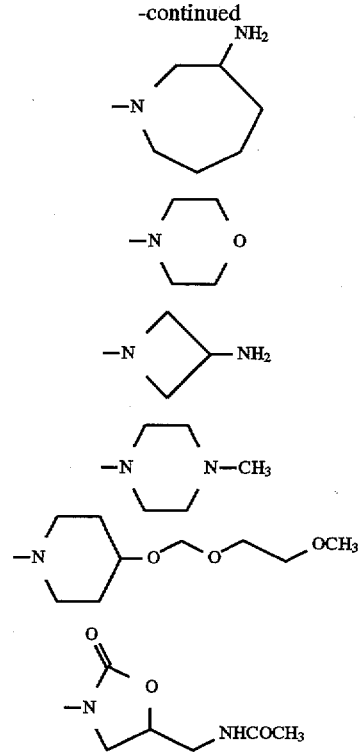

The compounds of the invention comprise asymmetrically substituted carbon atoms. Such asymmetrically substituted carbon atoms can result in the compounds of the invention comprising mixtures of stereoisomers at a particular asymmetrically substituted carbon atom or a single stereoisomer. As a result, racemic mixtures, mixtures of diastereomers, as well as single diastereomers of the compounds of the invention are included in the present invention. The terms "S" and "R" configuration, as used herein, are as defined by the IUPAC 1974 *Recommendations for Section E, Fundamental Stereochemistry, Pure Appl. Chem.* (1976) 45, 13–30. The terms α and β are employed for ring positions of cyclic compounds. The α-side of the reference plane is that side on which the preferred substituent lies at the lowered numbered position. Those substituents lying on the opposite side of the reference plane are assigned β descriptor. It should be noted that this usage differs from that for cyclic stereoparents, in which "α" means "below the plane" and denotes absolute configuration. The terms α and β configuration, as used herein, are as defined by the *Chemical Abstracts Index Guide-Appendix IV* (1987) paragraph 203.

Preferred compounds of the invention include compounds of the formula (II) having a backbone structure wherein X is oxygen, according to formula (III):

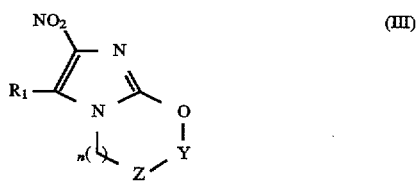

(III)

wherein $R_1$, Y, Z and n are as defined above, resulting in the following embodiments IIa, IIIb and IIIc when n is 1, 2 or 3, respectively:

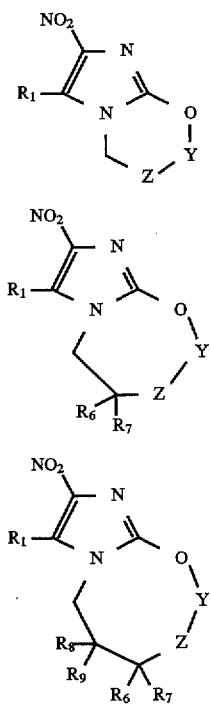

wherein $R_6$, $R_7$, $R_8$ and $R_9$ are as defined above; and the pharmaceutically acceptable salts thereof.

Even more preferred compounds of the invention include compounds of the formula (IV):

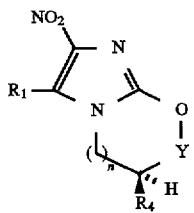

wherein $R_1$, $R_4$, n and Y are as defined above; and the pharmaceutically acceptable salts thereof.

The presently most preferred compounds of the invention include compounds of the formulas (IVa):

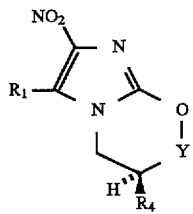

wherein $R_1$, $R_4$, n and Y are as defined above; and the pharmaceutically acceptable salts thereof.

The present invention also relates to the processes for preparing the compounds of the invention and to the synthetic intermediates useful in such processes, as described in detail below.

In yet a further aspect of the present invention, pharmaceutical compositions are provided which comprise a compound of the present invention in combination with a pharmaceutically acceptable carrier.

Figure 2:
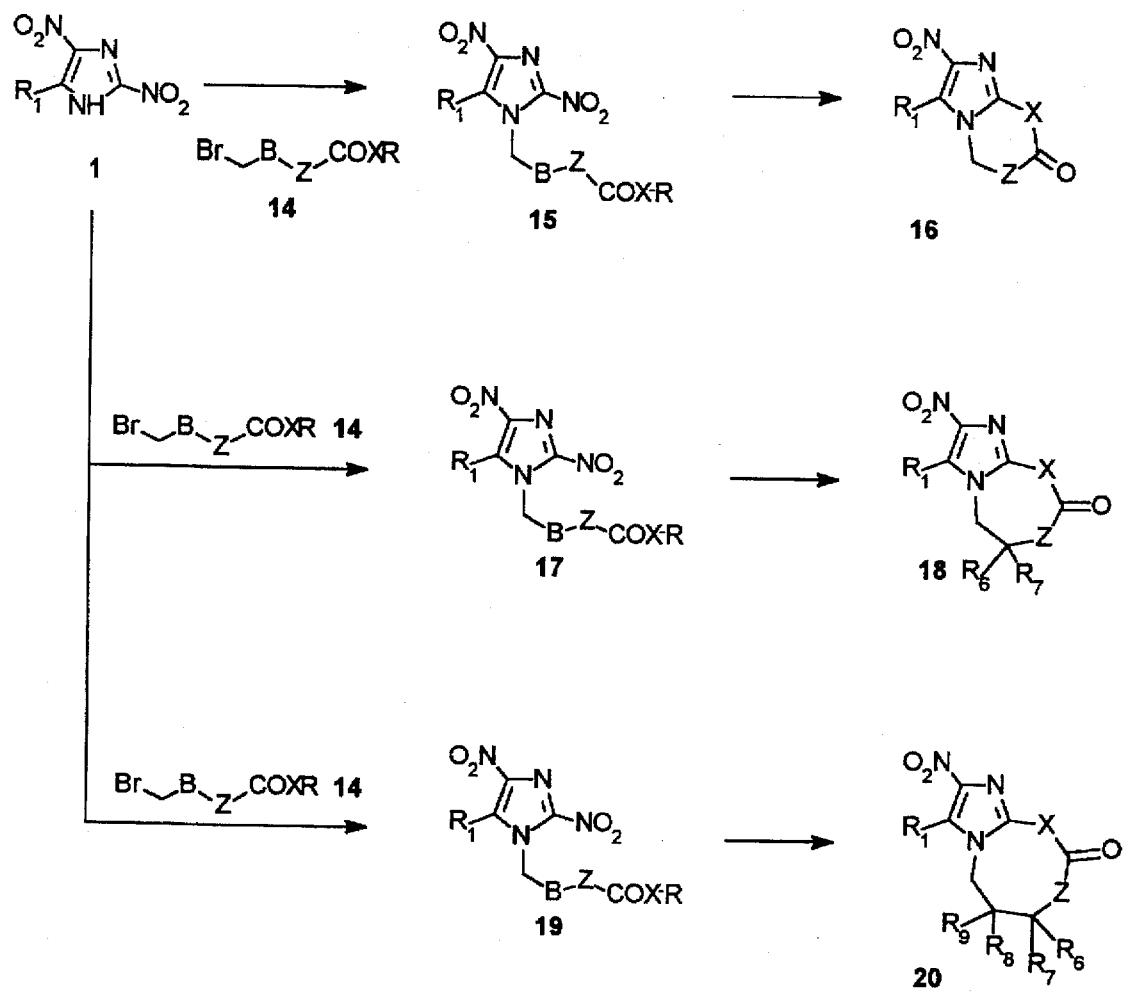
FIG. 2 is a schematic representation of further synthesis pathways of compounds of the invention.
Figure 4:
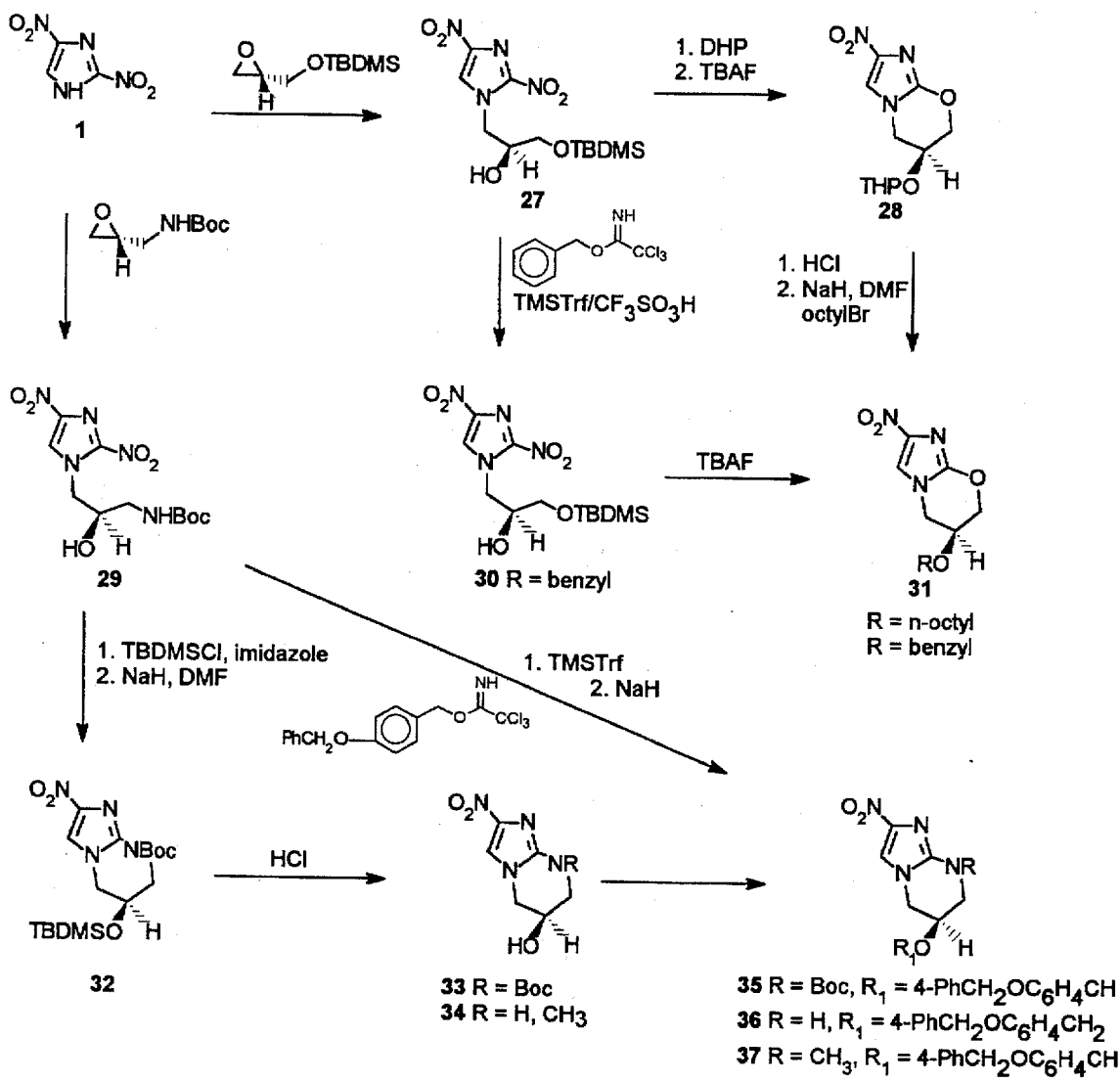
FIGS. 4 and 5 are schematic representations of alternative synthesis pathways of compounds of the invention.
Figure 5:
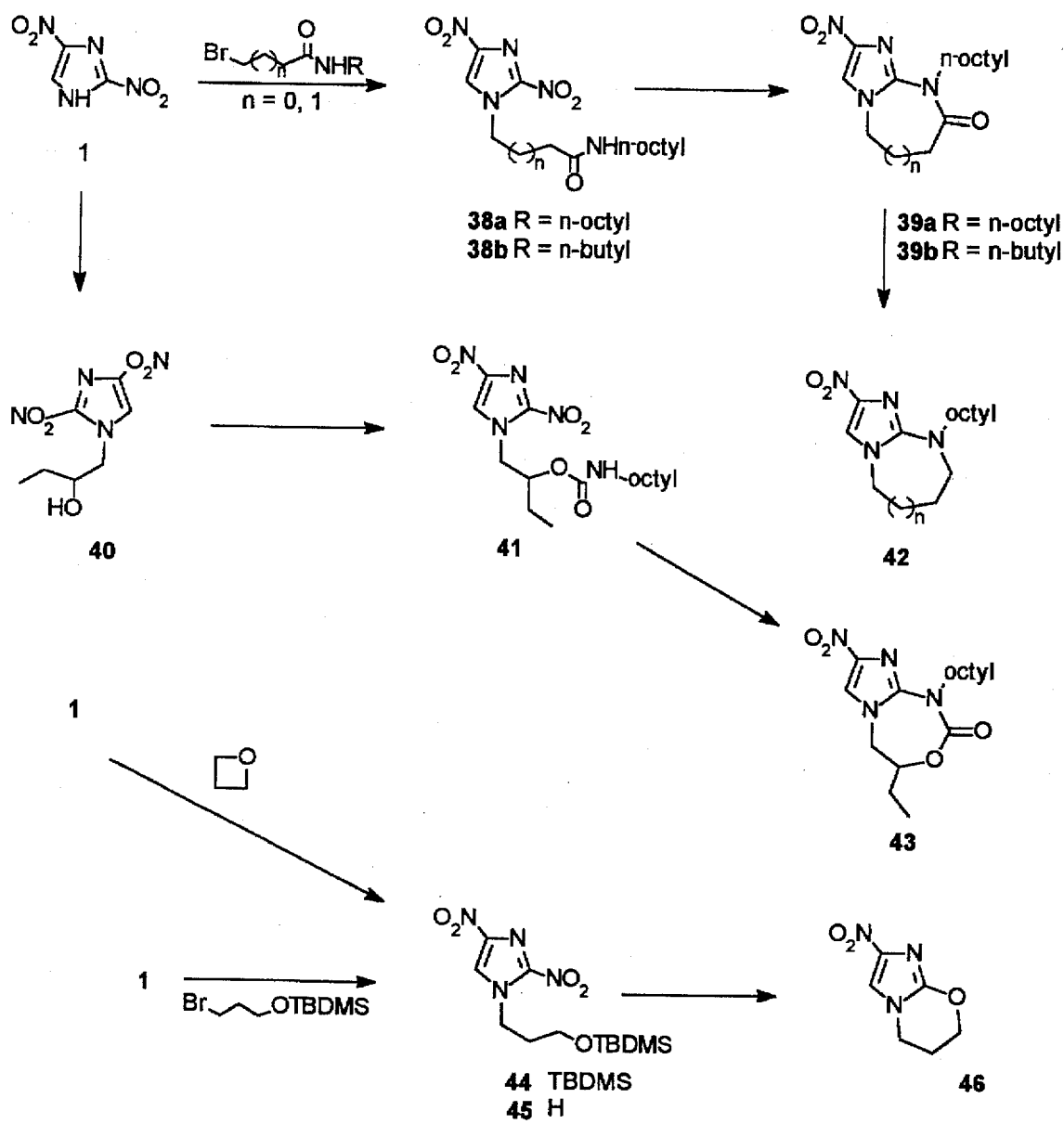

In general, the compounds of the invention can be prepared by the processes illustrated in Schemes I (FIGS. 1 and 2), II (FIG. 3), III (FIG. 4) and IV (FIG. 5). According to the reaction Scheme I, functionalized nitroimidazole compounds 4, 7, 10, 13, 16, 18, and 20 are prepared by three methods. The first method involves the alkylation of 2,4-dinitroimidazole (1, $R_1$=H, Ind. J. of Chem. 21B:1022–1026 (1982)) with epoxides 2 and 11 using a modified procedure of Agrawal et al., (J. Med. Chem. 24:601–604 (1981)) in which compound 1 and epoxides 2 or 11 are warmed to 70° C. as a neat solution and kept at 70° C. for several hours. The hydroxy dinitroimidazole products 3 (Z =$CR_2OH$) and 12 (X=OH) are isolated as solids by washing the reaction mixture with diethyl ether and aqueous sodium bicarbonate. The crude hydroxy imidazole 3 ($Z_1$=$CR_2OH$) is protected as an ether derivative selected from but not limited to 2-tetrahydopyranyl (THP), trimethylsilyl (TMS), t-butyldimethylsilyl (TBDMS), acetyl (Ac), benzyl (Bn), and 2,4-dimethoxybenzyl. The second method involves the alkylation of dinitroimidazole 1 with an alkyl halide 5 or 14 to produce substituted dinitroimidazole compounds 6, 15, 17 or 19. The third method utilized for the preparation of 1-alkyl-2,4-dinitroimidazole compounds involves reaction of 1 with electron poor olefins such as 8 (Z=CCN, $CCO_2Et$, $CSO_2R$) to give imidazoles 9. Removal of the $R_3$ protecting group from compounds 3, 6, and 9 affords an alcohol (X=OH), amine or amide (X=NR), or a mercaptan (X=SH). When X is a methylene or methine the $R_3$ group maybe present. The bicyclic nitroimidazole compounds 4, 7, 10, 13, 16, 18, and 20 are obtained by reaction of 3, 6, 9, 12, 15, 17, and 19 (X =OH, NHR, SH, CHR, X=OCONHR, Y=CO or $CR_1R_2$) with bases such as sodium hydride, potassium t-butoxide, cesium fluoride, tetrabutylammonium fluoride (TBAF) and the like in an inert and dry organic solvent such as dimethylformamide (DMF), tetrahydrofuran (THF), dimethoxyethane (DME).

Figure 3:
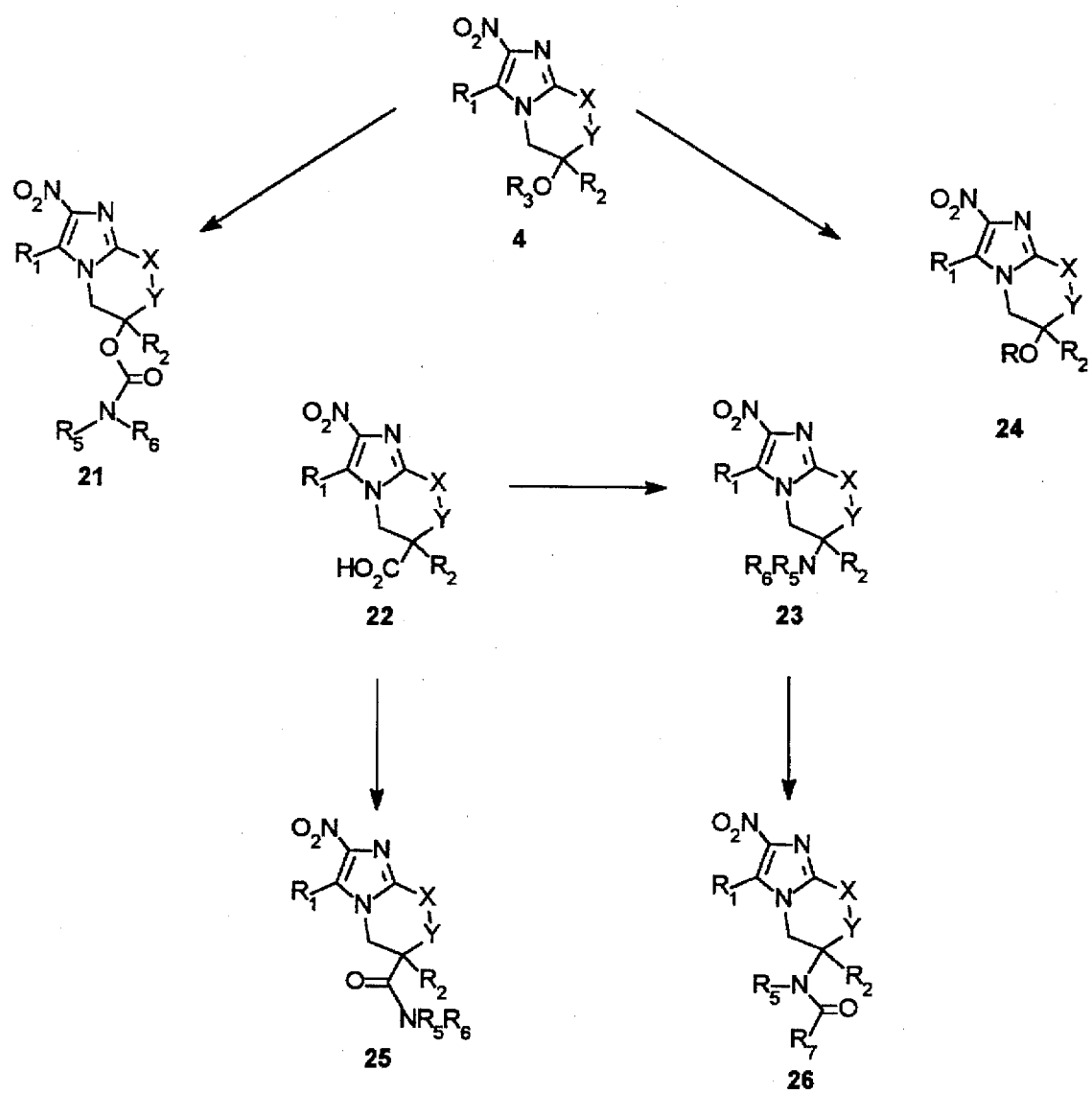
FIG. 3 is a schematic representation of alternative synthesis pathway of compounds of the invention.

Referring now to FIG. 3, the preparation of bicyclic nitroimidazole alcohol derivatives are shown in Scheme II. Deprotection of 4 (for example R=THP) with acetic acid in aqueous THF at room temperature to reflux temperature for several hours gives alcohol 4 ($R_3$=H) which can be reacted with a variety of acylating and alkylating reagents to produce analogs 21 and 24. For example, the carbamate compound 21 is prepared by reacting 4 ($R_3$=H) with carbonyldiimidazole (CDI) and a base such as diazabicycloundecene (DBU), sodium hydride, potassium t-butoxide, sodium bis(trimethylsilyl)amide and the like in an inert and dry solvent. The resulting acylimidazole intermediate 4 ($R_3$=C=Oimidazole) is reacted with a primary or secondary amine to give the carbamate. The ether analogs 24 are prepared by reacting alcohol 4 ($R_3$=H) with a variety of alkylating reagents selected from but not limited to methyl iodide, octyl iodide, benzyl bromide, 4-benzyloxybenzyl chloride, 4-butylbenzyl bromide and the like with strong bases such as sodium hydride, potassium hydride, sodium bis(trimethylsilyl)amide in a dry aprotic solvent at temperatures between –20° C. to 70° C. The synthesis of the amino and amides derivatives, 23 and 25 or 26, respectively, proceeds through the common intermediate, carboxylic acid, 22. Reaction of 1 with the TBDMS ether of ethyl α-(hydroxymethyl)acrylate (8, R=H, Org. Synthesis 1987, 66, 220) in the presence of a base, for example, sodium ethoxide in ethanol, and deprotection of the silyl ether with tetrabutylammonium fluoride in THF gives the ethyl ester 10 (Z=$CHCO_2Et$, X=O, Y=$CH_2$). The ester is hydrolyzed using an alkaline base such as sodium hydroxide, lithium hydroxide in water, aqueous ethanol, THF, dioxane and the like. The resulting carboxylic acid 22 is reacted with triethylamine and diphenylphosphorylazide in toluene at 70° to 150° C. to give an isocyanate intermediate. Reaction of an alcohol or amine with the isocyanate gives the carbamate 26 ($R_5$=H, $R_7$=RO) or urea 26 ($R_5$=H, $R_7$=$RR_1$N), respectively. When the intermediate isocyanate is reacted with t-butanol the product carbamate 26 ($R_5$=$R_7$=t-BuO) is isolated. Alkylation of the t-butyl carbamate with electrophiles such as an alkyl or alkylaryl halide and the like and deprotection of the Boc (t-butyl carbamate) group with trifluoroacetic acid, or hydrochloric acid gives the secondary amine 23 ($R_5$=H, $R_6$=alkyl, alkylaryl). Alternatively, the Boc carbamate 26 ($R_5$=H, $R_7$=t-BuO) is reacted with trifluoroacetic acid, or hydrochloric acid to give the primary amine 23 ($R_5$=$R_6$=H) which can be reductively alkylated (RCHO, sodium cyanoborohydride) to give the secondary amine 23 ($R_5$=H, $R_6$=$RCH_2$). A second alkylation of the secondary amine with an electrophile such as an alkyl or alkylaryl halide and the like gives a tertiary amine 23 ($R_5$=$R_6$=alkyl, alkylaryl). Additional reactions that the primary or secondary amine 23 ($R_5$=$R_6$=H or $R_5$=H, $R_6$=alkyl, alkylaryl) undergo include acylation with an acid chloride, sulfonyl chloride, isocyanate, and isothiocyanate to give derivative 26 ($R_5$=H or alkyl, alkylaryl, $R_7$=alkyl, alkylaryl, aryl, heterocycle ), 23 ($R_5$=H or alkyl, alkylaryl, $R_6$=$SO_2$alkyl, $SO_2$alkylaryl, $SO_2$aryl, $SO_2$heterocycle), 26 ($R_5$=H or alkyl, alkylaryl, $R_7$=NHalkyl, NHheterocycle), and 23 ($R_5$=H or alkyl, alkylaryl, $R_6$=alkylNHC=S, alkylarylNHC=S, arylNHC=S, heterocycleNHC=S). The synthesis of carboxamide derivatives 25 was accomplished by reaction of acid 22 and a primary or secondary amine with a peptide coupling reagent, such as hydroxybenzotriazole (HOBT)/dicyclohexylcarbodiimide (DCC) or 2-[1H-benzotriazole-1-yl]-1,13,3,tetramethyluronium hexafluorophosphate (HBTU) and the like. The peptide coupling reaction may be conducted in a polar aprotic solvent (for example, dimethylformamide and N-methylpyrrolidone (NMP) with a base such as N-methylmorpholine and the like).

Referring now to FIGS. 4 and 5, specific compounds of the invention are prepared according to the procedures outlined in Schemes III and IV. Keaction of 2,4-dinitroimidazole (1, 1 eq.) with of K-glycidol TBDMS ether (2 eq.) (Example 1) as a neat solution at 70° C. gave the hydroxy imidazole 27. Protection of the alcohol as its trahydropranyl ether (DHP, p-TsOH) and desilylation of the TBDMS group with tetrabutylammonium fluoride produced the bicyclic nitroimidazole THP ether 28. Deprotection of the THP group was effected using acetic acid in aqueous THF and the resulting alcohol was alkylated with octyl bromide and sodium hydride in DMF at room temperature. The octyl ether 31 (K=octyl) was obtained as a white crystalline solid ($[\alpha]^{25}D$=−28.1°). Synthesis of the entiomefic ether series was also acheived and ent-31 (R=octyl) was obtained ($[\alpha]^{25}D$=+27.45°). Alternatively, alcohol 27 was alkylated with benzyltrichloroacetimidate and TMS triflate or triflic acid according to the procedure of D. R. Bundle et al., *J. Chem. Soc.* Perkin Trans. I, 11:2247–2250 (1985) to give the benzyl ether 30 (R=benzyl). Treatment of the TBDMS ether 30 (R=benzyl) with TBAF cleaved the silyl group with concomitent cyclization to give 31 (R=benzyl). Synthesis of the nitrogen-containing bicyclic nitroimidazole analog 37 was accomplished using a similiar approach. Thus, reaction of 1 with the Boc epoxide gave 29. Protection of alcohol 29 as the TBDMS ether (TBDMSCl, imidazole, DMF) and cyclization of the resulting Boc amino ether with sodium hydride in DMF gave imidazole 32. Both the Boc and TBDMS protecting groups were removed by treating compound 32 with aqueous HCl. The amino alcohol was selectively alkylated (sodium hydride, methyl iodide, DMF) to give the N-methyl derivative 34 (R=$CH_3$) which was alkylated in a second step (sodium hydride, 4-benzyloxybenzyl chloride, DMF, 0° C. to room temperature) affording the aza nitroimidazole compound 37. Alkylation of the secondary alcohol in 29 with 4-benzyloxybenzyltrichloroacetimidate and trimethylsilyl triflate proceeded smoothly. Sodium hydride assisted cyclization as previously described gave compound 35. Removal of the Boc group using standard conditions (trifluoroacetic acid/dichloromethane) and alkylation of the resulting amine (methyl iodide, sodium iodide) afforded 37. Scheme IV illustrates the preparation of cyclic lactams 39, aza analog 42, cyclic carbamate 43 and pyran 46 derivatives. 3-Bromopropionamide and 4-bromobutramides reacted with the sodium salt of 1 in DMF to give the acyclic amides 38. The cyclic amides 39a and 39b were obtained by treating 38a and 38b with sodium hydride in DMF. Reduction of the carbonyl group of 39a was affected with borane in THF at reflux temperature, affording the aza derivative 42 in good yield. The cyclic carbamate 43 was prepared by reacting alcohol 40 with octyl isocyanate in the presense of CuI to give carbamate 41 which was cyclized under basic conditions (sodium hydride, DMF). Finally, the pyranyl nitroimidazole analog 46 was prepared either by alkylation of 1 with the bromo TBDMS ether followed by deprotective cyclization or opening oxetane with 1 in the presense of lithium tetrafluoroborate in THF followed by base (sodium hydride, DMF) induced cyclization of alcohol 45.

The compounds of the present invention can be used in the form of salts derived from inorganic or organic acids. These salts include but are not limited to the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxyethanesulfonate, lactate, maleate, methanesulfonate, nicotinate, 2-napthalenesulfonate, oxalate, pamoate, pectinate, persulfate, 3-phenylproionate, pierate, pivalate, propionate, succinate, tartrate, thiocyanate, p-toluenesulfonate and undecanoate. Also, the basic nitrogen-containing groups can be quatemized with such agents as loweralkyl halides, such as methyl, ethyl, propyl, and butyl chloride, bromides, and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Examples of acids which may be employed to form pharmaceutically acceptable acid addition salts include such inorganic acids as hydrochloric acid, sulphuric acid and phosphoric acid and such organic acids as oxalic acid, maleic acid, succmic acid and citric acid. Basic addition salts can be prepared in situ during the final isolation and purification of the compounds of formula (I), or separately by reacting carboxylic acid moieties with a suitable base such as the hydroxide, carbonate or bicarbonate of a pharmaceutical acceptable metal cation or with ammonia, or an organic primary, secondary or tertiary amine. Pharmaceutical acceptable salts include, but are not limited to, cations based on the alkali and alkaline earth metals, such as sodium, lithium, potassium, calcium, magnesium, aluminum salts and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like. Other representative organic amines useful for the formation of base addition salts include diethylamine, ethylenediamine, ethanolamine, diethanolamine, piperazine and the like.

The compounds of the invention are useful in vitro in inhibiting the growth of pathogenic mycobacteria, and in vivo in human and animal hosts for treating pathogenic mycobacterial infections, including tuberculosis. The compounds may be used alone or in compositions together with a pharmaceutically acceptable carrier.

Total daily dose administered to a host in single or divided doses may be in amounts, for example, from 0.001 to 1000 mg/kg body weight daily and more preferred from 1.0 to 30 mg/kg body weight daily. Dosage unit compositions may contain such amounts of submultiples thereof to make up the daily dose.

The amount of active ingredient that may be combined with the carrier materials to produce a single dosage form will vary depending upon the host treated and the particular mode of administration.

It will be understood, however, that the specific dose level for any particular patient will depend upon a variety of factors including the activity of the specific compound employed, the age, body weight, general health, sex, diet, time of administration, route of administration, rate of excretion, drug combination, and the severity of the particular disease undergoing therapy.

The compounds of the present invention may be administered orally, parenterally, sublingually, by inhalation spray, rectally, or topically in dosage unit formulations containing conventional nontoxic pharmaceutically acceptable carriers, adjuvants, and vehicles as desired. Topical administration may also involve the use of transdermal administration such as transdermal patches or ionophoresis devices. The term parenteral as used herein includes subcutaneous injections, intravenous, intramuscular, intrasternal injection, or infusion techniques.

Injectable preparations, for example, sterile injectable aqueous or oleagenous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1/3-propanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or di-glycerides. In addition, fatty adds such as oleic acid find use in the preparation of injectables.

Suppositories for rectal administration of the drug can be prepared by mixing the drug with a suitable nonirritating excipient such as cocoa butter and polyethylene glycols which are solid at ordinary temperatures but liquid at the rectal temperature and will therefore melt in the rectum and release the drug.

Solid dosage forms for oral administration may include capsules, tablets, pills, powders, and granules. In such solid dosage forms, the active compound may be admixed with at least one inert diluent such as sucrose lactose or starch. Such dosage forms may also comprise, as is normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting agents, emulsifying and suspending agents, and sweetening, flavoring, and perfuming agents.

The compounds of the present invention can also be administered in the form of liposomes. As is known in the art, liposomes are generally derived from phospholipids or other lipid substances. Liposomes are formed by mono- or multilameliar hydrated liquid crystals that are dispersed in an aqueous medium. Any nontoxic, physiologically acceptable and metabolizable lipid capable of forming liposomes can be used. The present compositions in liposome form can contain, in addition a compound of the present invention, stabilizers, preservatives, excipients, and the like. The preferred lipids are the phospholipids and phosphatidyl oholines (lecithins), both natural and synthetic. Methods to form liposomes are known in the art. See, for example, Prescott, Ed., *Methods in Cell Biology*, Volume XIV, Academic Press, New York, N.W. (1976), p.33 et seq.

While the compounds of the invention can be administered as the sole active pharmaceutical agent, they can also be used in combination with one or more other agents used in the treatment of pathogenic mycobacterial infections. Kepresentative agents useful in combination with the compounds of the invention for the treatment of *M. tuberculosis* include, for example, isoniazid, rifampin, pyrazinamide, ethambutol, rifabutin, streptomycin, ciprofloxacin and the like.

The above compounds to be employed in combination with the nitroimidazole compounds of the invention will be used in therapeutic amounts as indicated in the PHYSICIANS' DESK REFERENCE (PDK) 47th Edition (1993), which is incorporated herein by reference, or such therapeutically useful amounts as would be known to one of ordinary skill in the art.

The compounds of the invention and the other antiinfective agent can be administered at the recommended maximum clinical dosage or at lower doses. Dosage levels of the active compounds in the compositions of the invention may be varied so as to obtain a desired therapeutic response depending on the route of administration, severity of the disease and the response of the patient. The combination can be administered as separate compositions or as a single dosage form containing both agents. When administered as a combination, the therapeutic agents can be formulated as separate compositions which are given at the same time or different times, or the therapeutic agents can be given as a single composition.

The foregoing may be better understood by reference to the following examples, which are provided for illustration and are not intended to limit the scope of the inventive concepts.

EXAMPLE 1

(3S) 1-(2'-Hydroxy-3'-t-butyldimethylsilyloxy)-propyl-2,4-dinitroimidazole

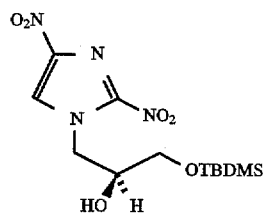

A mixture of 1.93 g (10.5 mmol) of (S)-glycidol tert-butyl dimethylsilyl ether (Liu, H. et al. *J. Org. Chem.*, 57:2471 (1992)) and 1.11 g (7.0 mmol) of 2,4-dinitroimidazole in EtOH (0.5 mL), was heated at 70° C. for 18 hours. The mixture was cooled and directly added to a silica gel column. The product was purified using EtOAc/Hexane (1:4) as the eluant, to give 1.28 g (53%) (3S) 1-(2'-hydroxy-3'-t-butyldimethylsilyloxy)-propyl-2,4-dinitroimidazole as a yellow oil: $^1$H NMR (DMSO): δ8.60 (s, 1H), 5.27 (d, 1H), 4.65 (dd, 1H), 4.27 (dd, 1H), 3.96 (m, 1H), 3.60 (dd, 1H), 3.44 (m, 1H), 0.82 (s, 9H), 0.03 (s, 6H); MS 347 (M+ff)$^+$

EXAMPLE 2

3S-Tetrahydopyranyloxy-6-nitro-2H-3,4-dihydro-[2-1b]imidazopyran

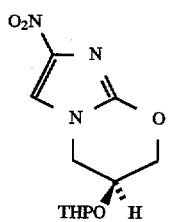

A solution of the compound prepared in Example 1 (1.24 g, 3.6 mmol), 3,4-dihydro-2H-pyran (0.61 g, 7.16 mmol), and 1.35 g (5.37 mmol) of pyridinium p-toluene sulfonate in CH$_2$C$_{12}$ (20 mL) was stirred for 20 hours at room temperature. The reaction mixture was washed with saturated NaHCO$_3$ and water. The organic layer was dried (MgSO$_4$) and the solvent evaporated. Purification of the residue by silica gel chromatography using hexane:EtOAc (10:1) as the eluant gave 1.21 g of the intermediate THP-protected ether in 79% yield.

To a solution of 1.21 g (2.81 mmol) of the THP ether in dry THF (10 mL) was added 8.4 mL (8.4 mmol) of tetrabutylammonium fluoride (1.0M solution in THF) dropwise. The reaction mixture was allowed to stir for 1 hour, after which the solvent was evaporated. The residue was diluted with CHCl$_3$ and washed with saturated NaHCO$_3$ and water. The organic extracts were dried (MgSO$_4$) and the solvent evaporated. The crude mixture was subjected to column chromatography, using EtOAc:MeOH (97:3) as the eluant, giving 0.55 g (73%) of the title compound: mp 138°–139° C.; $^1$H NMR (CDCl$_3$): δ7.42 (s, 1H), 4.85 (s, 1H), 4.10–4.60 (m, 4H), 3.54–3.87 (m, 2H), 1.58 (m, 6H); MS 431 (M+H)$^+$.

EXAMPLE 3

3S-Hydroxy-6-nitro-2H-3,4-dihydro-[2-1b]imidazopyran

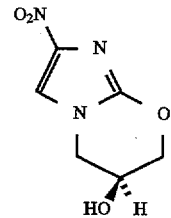

A solution of 4.06 g (15 mmol) of the THP ether prepared in Example 2 in dry THF (32 mL), water (16 mL) and acetic acid (64 mL) was heated at 45° C. for 18 hours. The reaction mixture was concentrated and the residue was recrystallized from boiling MeOH to give 2.18 g (79%) of the title compound: mp 220° C. (dec.); $^1$H NMR (DMSO): δ8.07 (s, 1H), 5.69 (s, 1H), 4.17–4.39 (m, 4H), 3.98 (d, 1H); MS 186 (M+H)$^+$.

EXAMPLE 4

3S-nOctyloxy-6-nitro-2H-3,4-dihydro-[2-1b]imidazopyran

General Procedure for the Alkylation of Alcohol 4 (R3=H) with Alkyl Halides

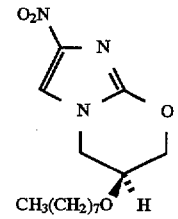

To a solution of 1.03 g (5.55 mmol) of the alcohol prepared in Example 3 in dry DMF (7 mL), at 0° C., was added 0.26 g (6.66 mmol) of NaH (60% in oil). After 0.5 hours of stirring, 1.03 mL (5.68 mmol) of 1-iodooctane was added and the reaction mixture was stirred at room temperature for 20 hours. The reaction was quenched with water and extracted with EtOAc. The organic extracts were dried (MgSO$_4$) and the solvent evaporated. The residue was subjected to column chromatograpy (hexane:EtOAc) to give 0.49 g (30%) of the title compound: mp 108°–109° C.; [α]$^{25}$D (CHCl$_3$, c=0.1)=−28.1° ; $^1$H NMR (CDCl$_3$): δ7.41 (s, 1H), 4.55 (dd, 1H), 4.00–4.35 (m, 4H), 3.56 (m, 2H), 1.59 (m, 4H), 1.25 (br s, 8H), 0.87 (m, 3H); MS 298 (M+H)$^+$. Anal. cated. for C$_{14}$H$_{23}$N$_3$O$_4$:C, 56.55; H 7.80; N, 14.13. Found: C, 56.66; H, 7.97; N, 14.00.

EXAMPLE 5

(3R) 1-(2'-Hydroxy-3'-t-butyldimethylsilyloxy)-propyl-2,4-dinitroimidazole

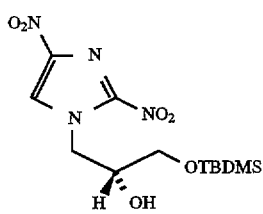

The procedure described in Example 1 was repeated substituting (R) gylcidol t-butyldimethylsilyl ether for (S) gylcidol t-butyldimethylsilyl to yield (3R) 1-(2'-hydroxy-3'-t-butyldimethylsilyloxy)propyl-2,4-dinitroimidazole. $^1$H NMR (CDCl$_3$) δ0.13 (s, 6H), 0.94 (s, 9H), 3.07 (d, 1H), 3.75 (d, 2H), 4.13 (m, 1H), 4.53 (dd, 1H), 4.85 (dd, 1H), 8.11(s, 1H); $^{13}$C NMR (CDCl$_3$) δ19.21, 26.77, 54.78, 65.02, 70.90, 125.96.

EXAMPLE 6

3R-Tetrahydopyranyloxy-6-nitro-2H-3,4-dihydro-[2-1b]imidazopyran

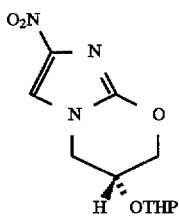

The title compound was prepared using the procedure outlined in Example 2 and substituting the product from Example 5 for the alcohol prepared in Example 1 to give the cyclic THP ether. mp 145°–146° C.; $^1$H NMR (DMSO) δ1.43 (m, 4H), 1.65 (m, 2H), 3.49 (m, 1H), 3.63 (m, 1H), 4.18–4.70 (m, 5H), 4.90 (m, 1H), 8.02, 8.05 (ss, 1H); $^{13}$C NMR (DMSO) δ20.36, 20.25, 26.21, 26.25, 31.54, 31.61, 47.87, 49.61, 63.25, 63.43, 65.58, 65.72, 69.33, 71.44, 98.29, 98.45, 119.38, 119.45, 148.57.

EXAMPLE 7

3R-Hydroxy-6-nitro-2H-3,4-dihydro-[2-1b] imidazopyran

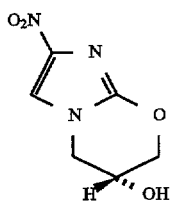

3R-hydroxy-6-nitro-2H-3,4-dihydro-[2-1b]imidazopyran was prepared using the procedure outlined in Example 3 and the product from Example 6 for the THP ether prepared in Example 2: mp 208° C. (decomposed); $^1$H NMR (DMSO) δ3.96 (d, 1H), 4.16–4.43 (m, 4H), 5.68 (d, 1H), 8.06 (s, 1H); $^{13}$C NMR (DMSO) δ50.70, 60.52, 72.22, 119.53, 143.58, 148.62.

EXAMPLE 8

3R-nOctyloxy-6-nitro-2H-3,4-dihydro-[2-1b] imidazopyran

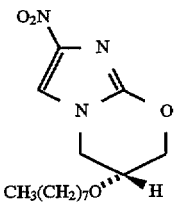

3R-n-octyloxy-6-nitro-2H-3,4-dihydro-[2-1b] imidazopyran was prepared using the general alkylation procedure outlined in Example 4 and the product from Example 8: mp 104°–106° C.; 8.06 (CHCl$_3$, c=1) +27.45° ; $^1$H NMR (DMSO) δ0.83 (t, 3H), 1.25 (m, 12H), 1.44 (m, 2H), 3.53 (q, 2H), 4.08 (q, 1H), 4.18 ppm (d, 2H, 4.49 (q, 2H, 8.03 (s, 1H; $^{13}$C NMR (DMSO) δ15.35, 23.51, 26.94, 30.13, 30.50, 32.65, 48.07, 67.92, 69.37, 69.46, 119.38, 143.53, 148.57; MS 98 (M+H). Anal. calcd. for C$_{14}$H$_{23}$N$_3$O$_4$: C, 56.55; H, 7.80; N, 14.13. Found: C, 56.37; H, 7.86; N, 13.97.

EXAMPLE 9

1-(2'-Hydroxy-3'-N-tert-butyloxycarbonyl)-propyl-2,4-dinitro imidazole

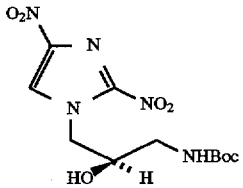

EXAMPLE 9A

N-(tert-butyloxycarbonyl)-allylamine epoxide

A solution of 5.72 gram (0.1 mol) of allylamine was added dropwise to a solution of 130 mL freshly distilled tetrahydrofuran (THF) and 28.4 gram (0.13 mol) di-tert-butyl dicarbonate under N$_2$ at room temperature. After three hours the solvent was removed by rotary evaporation and the Boc amine was obtained as a clear oil: $^1$H NMP, (CDCl$_3$) δ5.91–5.78 (m, 1H), 5.21–5.10 (m, 2H), 4.65 (broad s, 1H), 3.75 (broad s, 2H), 1.45 (s, 9H), indicated desired product was synthesized.

To the crude N-tert-butyloxycarbonylallylamine in 700 mL of dichloromethane was added 63 g (0.44 ml) of anhydrous sodium phosphate dibasic and 84 g (0.489 mol) m-chloroperbenzoic acid. The reaction was stirred mechanically for 24 hours and quenched with saturated sodium bicarbonate and saturated sodium thiosulfate (Na$_2$S$_2$O$_3$) and extracted three times of dichloromethane. The combined organic extracts were dried over magnesium sulfate and concentrated under reduced pressure. Chromatography on silica gel eluting with CH$_3$OH:CHCl$_3$ (1:4) gave N-(tert-butyloxycarbonyl)allylamine epoxide in 60% yield (10.3 g): $^1$H NMR (CDCl$_3$) δ4.95 (broad s, 1H), 3.57–3.50 (broad m, 1H), 3.26–3.15 (m, 1H), 3.09 (m, 1H), 2.79–2.76 (t, 1H, 1=4.2 Hz), 2.60–2.58 (dd, 1H, J=2.7, 4.8 Hz).

EXAMPLE 9B 1-(2'-hydroxy-3'-N-tert-butyloxycarbonyl)-propyl 2,4-dinitroimidazole A mixture of 158 mg (1 mmol) 2,4-dinitroimidazole and 885 mg (5 mmol) N-(tert-butyloxycarbonyl)allylamine epoxide were stirred under N: for 19 hours. Chromatography on silica gel using acetone:hexane (1:2) gave the title compound in 41% yield: $^1$H NMR. (CDCl$_3$) δ8.21 (s, 1H), 5.49 (broad s, 1H), 4.85 (d, 1H, J=13.2 Hz), 4.55–4.53 (m, 2H), 4.15 (broad s, 1H), 3.37 (broad m, 2H), 1.41 (s, 9H); MS (M+H)$^+$332.

EXAMPLE 10

N-tertButylcarbonyloxy 3S-tert-butyldimethylsilyloxy-6-nitro-1,2,3,4-tetrahydro-[2-1b]imidazopyrimidine

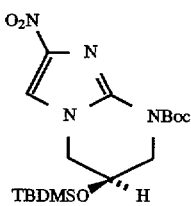

EXAMPLE 10A 1-(2'-hydroxy-3'-N-tert-butyloxycarbonyl)-propyl 2,4-dinitroimidazole TBDMS Ether To a mixture of imidazole (1.32 g, 34.3 mmol) in 30 mL of dry dimethyl formamide (DMF) and 1.82 g (5.5 mmol) of the compound prepared in Example 9B was added a solution of 2.20 g (14.6 mmol) of tert-butyldimethylsilyl chloride in 20 mL dry DMF. After 48 hours, an equal volume of ether was added and the mixture was washed three times with 0.5M HC1, two times with saturated sodium bicarbonate and once with brine. The organic solution was dried over anhydrous sodium sulfate, filtered, and concentrated under reduced pressure. Chromatography on silica gel using acetone:hexane (1:4) gave the title compound in 93% yield: mp 47.0°–49.5° C.; $^1$H NMR (CDCl$_3$) δ8.01 (s, 1H), 4.83–4.78(m, 2H), 3.22–3.17(m, 1H), 1.47(s, 9H), 0.85(s, 9H), 0.04(s, 3H), –0.24(s, 3H).

EXAMPLE 10B

N-tert-butylcarbonyloxy 3S-tert-butyldimethylsilyloxy-6-nitro-1,2,3,4-tetrahydro- [2-1b]imiidazopyrimidine To a solution of 5.11 g (11.5 mmol) of TBDMS ether prepared in Example 10A in 100 mL of dry DMF cooled at 0° C. was added 1.0 g (25 mmol, 60%) sodium hydride in portions. Once addition was completed, an additional 15 minutes at 0° C. was allowed before the reaction mixture was warmed slowly to room temperature. Four hours later, the reaction was quenched with water, the mixture was extracted with ether:toluene (1:1). The combined organic layers were dried, filtered, and evaporated. The crude residue was purified by silica gel chromatography (acetone:hexane, 1:4) to give the title compound in 51% yield: mp 59.5°–61.3° C.; $^1$H NMR (CDCl$_3$) δ7.52(s, 1H), 4.37–4.33 (m, 1H), 4.19–4.14 (dd, 1H, J=3.55, 12.88 Hz), 4.12–4.05 (qd, 1H, J=1.63, 4.75, 13.43 Hz), 3.91–3.86 (m, 1H), 3.57–3.52 (dd, 1H, J=1.63,13.42 Hz), 1.47(s, 9H), 0.77(s, 9H), 0.05(s, 3H), 0.04(s, 3H).

EXAMPLE 11

3R-Hydroxy-6-nitro-1,2,3,4-tetrahydro-[2-1b]imidazopyrimidine

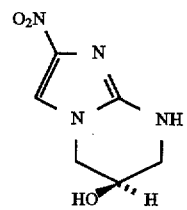

A solution of 21.2 mg (49 nmol) of TBDMS ether that was prepared in Example 10B in 5 ml of THF was added 1 ml of 2N HCl. After stirring the reaction at room temperature for 18 hours, the mixture was concentrated to dryness, dissolved in CHCl$_3$, and was purified on a silica gel column (CH$_3$OH:CH$_2$Cl$_2$ 1:4) to give 9.2 mg (85.0% yield) of 3R-hydroxy-6-nitro-1,2,3,4-tetrahydro-[2-1b] imidazopyrimidine as a yellow solid: mp 122° C. (decomposed); $^1$H NMR (D$_2$O) δ8.05 (brs, 1H), 4.51(m, 1H), 4.20 (brs, 2H), 3.55 (brs, 2H).

EXAMPLE 12

3R-Hydroxy-1-methyl-6-nitro-1,2,3,4-tetrahydro-[2-1b]imidazopyrimidine

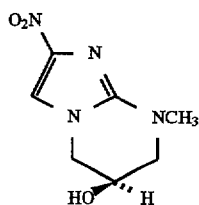

A DMF solution of the amino alcohol prepared in Example 11 is cooled to 0° .C and 1 equivalent of sodium hydride is added. The reaction mixture is stirred for min, 2 equivalents of methyl iodide are added and the reaction mixture is warmed to room temperature and stirred an additional 1 hour. Water is added, and 3R-hydroxy-1-methyl-6-nitro-1,2,3,4-tetrahydro-[2-1b]imidazopyrimidine is obtained by chloroform extraction.

EXAMPLE 13

3R-4-Benzyloxybenzyloxy-1-methyl-6-nitro-1,2,3,4-tetrahydro-[2-1b]imidazopyrimidine

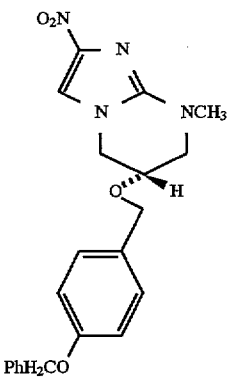

The general alkylation procedure described in Example 4 is followed and substituting the alcohol prepared in Example 12 for the alcohol prepared in Example 3, and substituting 4-benzyloxybenzyl chloride for n-octyl iodide gives 3R-4-benzyloxybenzyloxy-1-methyl-6-nitro-1,2,3,4-tetrahydro-[2-1b]imidazopyrimidine.

EXAMPLE 14

Octyl 4-(2,4-dinitroimidazoyl)butramide

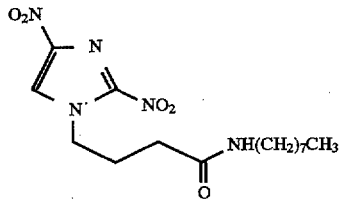

50–60% Sodium hydride (173 mg, 4.3 mmol) was added to a solution of 682 mg (4.3 mmol) of 2,4-dinitroimidazole in 4 mL of dry DMF. The mixture was stirred for 10 min at room temperature and 1 g (3.6 mmol) of N-octyl4-bromobutyramide in 2 ml dry DMF was added. The temperature of the reaction mixture was increased to 90° C. and the mixture was stirred for 18 hours. The reaction mixture was quenched with 100 mL of cold 0.005N HCl and extracted with ethyl acetate. The organic layer was washed with aqueous sodium bicarbonate, water and dried over anhydrous magnesium sulfate. The solvent was removed and the residue was purified on a silica gel column (hexane:ethyl acetate, 2:3) to give 1.04 g of octyl4-(2,4-dinitroimidazoyl)butramide in 81% yield. $^1$H MR (CDCl$_3$) δ0.80 (t, 3H), 1.19 (m, 12H), 1.41 (m, 2), 2.23 (m, 4H), 3.13 (m, 2H), 4.64 (t, 2H), 6.08 (t, 2H), 8.15 (s, 1H); $^{13}$C NMR (CDCl$_3$) δ15.02, 23.58, 26.67, 27.91, 30.16, 30.20, 30.50, 30.55, 32.73, 32.82, 40.72, 51.97, 125.62, 142.17, 144.10, 171.85; MS 356.1(M+H)$^+$.

EXAMPLE 15

Nitroimidazole Octyl Lactam

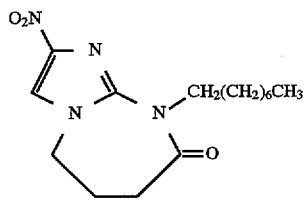

Sodium hydride 148 mg (3.66 mmol) was suspended in 30 ml of dry DMF and 650 mg (1.83 mmol) of the amide prepared in Example 14 in 10 ml dry DMF was added dropwise. The dark blue solution was stirred overnight at room temperature, and 100 mL of 0.005N HCl was added. The product was isolated by ethyl acetate extraction. The organic extracts were washed with sodium bicarbonate, water, and dried (MgSO$_4$). After removal of the solvent, the residue was purified by silica gel column chromatography (hexane:ethyl acetate, 2:3). The cyclic amide was obtained in 36% yield (204 mg). A sample was recrystallized from ethyl acetate/hexane to give the amide as light yellow needles: mp 92°–93° C.; $^1$H NMR (CDCl$_3$) δ0.86 (t, 3H), 1.24 (m, 10H), 1.57 (m, 2H), 2.42 (m, 2H), 2.48 (t, 2H), 3.94 (t, 2H), 4.13 (t, 2H), 7.73 (s, 1H); $^{13}$C NMR (CDCl$_3$) δ15.04, 23.56, 27.73, 28.12, 29.53, 30.11, 32.70, 33.76, 45.46, 47.92, 118.94, 144.16, 171.38; MS 309.1 (M+H)$^+$.

EXAMPLE 16

Nitroimidazole Octyl Azapine

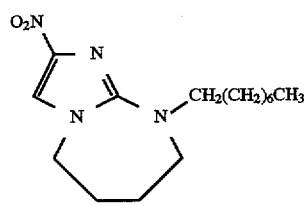

A solution of 0.2 mL (0.2 mmol) 1.0M borane in 5 mL of THF cooled in an ice-water bath was added 31 mg (0.1 mmol) of the amide prepared in Example 15. The mixture was heated at reflux temperature for 1.5 hour and cooled to room temperature. Decomposition of excess borane and borane complex was effected by the dropwise addition of concentrated HCl in water. After washing the aqueous HCl solution to remove neutral compounds, the water layer was treated with sodium bicarbonate and extracted with ethyl acetate. The extracts were dried over magnesium sulfate and the solvent concentrated. The product was purified by silica gel chromatography (hexane:ethyl acetate, 4:1) to give 10 mg of the reduced amide in 33%. $^1$H NMR (CDCl$_3$) δ0.86 (t, 3H), 1.24 (m, 10H), 1.57 (m, 2H), 1.88 (m, 2H), 3.06 (t, 3H), 3.40 (t, 2H), 3.94 (t, 2H), 7.55 (s, 1H); MS 296.1 (M+H)$^+$.

EXAMPLE 17

N-Octyl Carbamate of 1-(2 Õ-hydroxybutyl)-2,4-dinitroimidazole

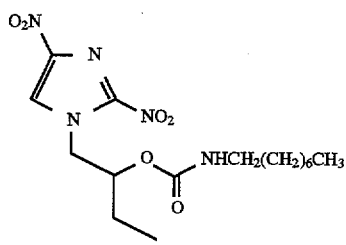

To a green heterogeneous mixture of 1-(2'-hydroxybutyl)-2,4-dinitroimidazole (500 mg, 2.17 mmol, Eur. J. Med. Chem. 24:631–633 (1989)) and 258 mg (2.60 mmol) of CuI in 10 mL of dry DMF was added 767 µL (4.34 mmol) of octyl isocyanate. The mixture was stirred for two hours, diluted with 40 mL of ethyl ether and the organic solution was washed with water, dried over magnesium sulfate and concentrated. The crude product was purified by chromatography on silica gel (hexane:ethyl acetate, 6:1) to give 502 mg (60%) of n-octyl carbamate. $^1$H NMR (CDCl$_3$) δ0.86 (t, 3H), 1.11 (t, 3H), 1.28(m, 10H), 1.40 (m, 2H), 1.75 (m, 2H), 3.05 (m, 2H), 4.42 (q, 1H), 4.75 (t, 1H), 4.90 (q, 1H), 5.10 (m, 1H), 7.88 (s, 1H); $^{13}$C NMR (CDCl$_3$) δ9.32, 14.01, 22.54, 25.10, 26.54, 29.06, 29.63, 31.69, 40.04, 41.08, 54.28, 72.65, 124.14, 155.20: MS 386 (M+)

EXAMPLE 18

Nitroimidazole Octyl Cyclic Carbamate

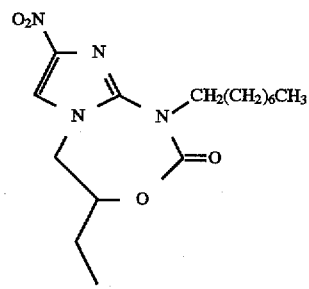

A solution of the compound prepared in Example 17 (500 mg, 1.30 mmol) in ml dry DMF and 50–60% sodium hydride (78 mg, 1.95 mmol) was stirred at room temperature for 1 hour. The reaction was quenched with 20 mL of 0.05N hydrochloric acid and extracted with ethyl acetate. The ethyl acetate extracts were washed with sodium bicarbonate, water and concentrated. The residue was purified by silica gel chromatography (hexane:ethyl acetate, 3:1) to give 260 mg of the cyclized carbamate (59% yield): mp 107°–109° C.; $^1$H NMR (CDCl$_3$) δ0.90 (t, 3H), 1.15 (t, 3H), 1.26 (m, 10H), 1.67–1.95 (m, 4H), 3.95–4.35 (m, 4H), 4.62 (m, 1H), 7.65 (s, 1H); $^{13}$C NMR (CDCl$^3$) δ9.48, 14.02, 22.55, 26.23, 26.62, 27.70, 29.06, 29.10, 31.68, 49.41, 50.54, 80.50, 117.59, 152.45; MS 338 (M+), 292.2 (M—NO$_2$:).

EXAMPLE 19

4-Benzyloxybenzyl Carbamate of 3R-Hydroxy-6-nitro-2H-3,4-dihydro-[2-1b]imidazopyran

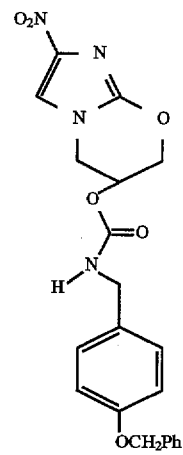

Using the procedure in Example 4, and substituting 1,1-carbonyldiimidazole for 1-iodooctane gave 13 mg (9% yield) of the acylimidazole: $^1$H NMR (DMSO) δ8.05 (s, 1H), 7.64 (s, 1H), 7.01 (s,2H), 5.36 (s, 1H), 4.61 (m,2H), 4.37(m,2H).

To a solution of the acylimidazole carbamate (1 eq.) in dry THF,4-benzyloxybenzylamine (1.1 eq., Pandey, G. D. et al., Pol. J. Chem. 54:763 (1980)) is added. After the reaction is complete, the 4-benzyloxybenzyl carbamate of 3R-hydroxy-6-nitro-2H-3,4-dihydro-[2-1b]imidazopyran is obtained.

EXAMPLE 20

3R-Carcoethoxy-6-nitro-2H-3,4-dihydro-[2-1b]imidazopyran

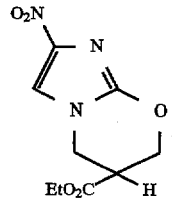

A solution of 2,4-dinitroimidazole (1 eq.), the TBS ether of ethyl α-(hydroxymethyl)acrylate (pl.1 eq., Org. Syn. 66:220 (1987)) and sodium ethoxide in ethanol is stirred at room temperature. Workup in the usual manner gives the product. Cyclization of the TBDMS ether intermediate is effected by reaction with tetrabutlyammonium fluoride as previously described.

EXAMPLE 21

3R-Carboxylate-6-nitro-2H-3,4-dihydro-[2-1b] imidazopyran

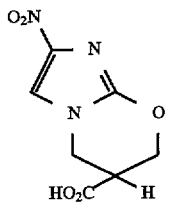

A solution of the ester prepared in example 20 and (1 eq.) of sodium hydroxide in EtOH is stirred at room temperature. After the completion of the reaction and acidic workup, 3R-carboxylate-6-nitro-2H-3,4-dihydro-[2-1b] imidazopyran is isolated by addition of HCl and ethyl acetate extraction.

EXAMPLE 22

4-Benzyloxybenzylamine Amide of 3R-Carboxylate-6-nitro-2H-3,4-dihydro-[2-1b] imidazopyran

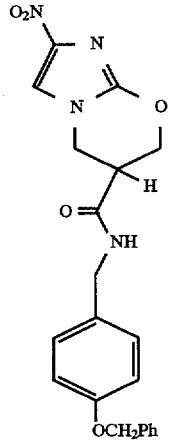

To a solution of the carboxylic acid prepared in Example 21 in DMF is added HBTU (2 eq.), 4-benzyloxybenzylamine (1.1 eq.), and N-methyl morpholine (NMM, 1.5 eq.). The 4-benzyloxybenzylamine amide of 3R-carboxylate-6-nitro-2H-3,4-dihydro-[2-1 b]imidazopyran is isolated isolated after workup and silica gel chromatography.

EXAMPLE 23

4-Benzyloxybenzamide of 3R-Amino-6-nitro-2H-3,4-dihydro-[2-1b]imidazopyran

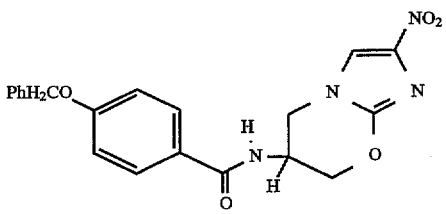

A solution of 3R-carboxylate-6-nitro-2H-3,4-dihydro-[2-1b]imidazopyran (Example 21, 1 eq.), triethylamine (1 eq.), diphenylphosphoryl azide (1 eq.) in toluene is heated at 80° C. for 4 h, cooled and t-butanol is added. The reaction is warmed to 70° C. for an additional 1 hour. Workup in the standard fashion gives the Bocamine. Deprotection of the Boc group (trifluoroacetic acid:dichloromethane, 1:1) and addition of 4-benzyloxybenzoyl chloride and triethylamine gives the 4-benzyloxybenzamide of 3R-amino-6-nitro-2H-3, 4-dihydro-[2-1b]imidazopyran.

EXAMPLE 24

N-Methyl, N-4-Benzyloxybenzyl 3R-Amino-6-nitro-2H-3,4-dihydro-[2-1b]imidazopyran

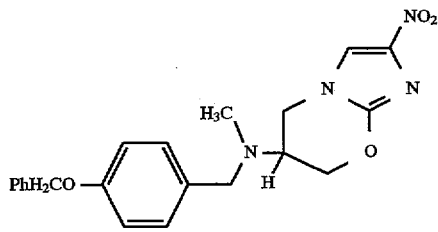

The N-Boc protected amine prepared in Example 23 is stirred with sodium hydride (1.1 eq.) and methyl iodide at 0° C. to room temperature. Following workup, the N-methyl amide is isolated. The Boc group is deprotected as described in Example 23 and the resulting methylamine is stirred with 4-benzyloxybenzaldehyde, sodium cyanoborohydride in methanol to give N-methyl, N-4-benzyloxybenzyl 3R-amino-6-nitro-2H-3,4-dihydro-[2-1b]imidazopyran.

EXAMPLE 25

Minium Inhibitory. Concentrations (MIC) of 3(R)-Alkoxy-6-nitro-2H-3,4-dihydro[2-1b]imidazopyran Antibacterial Compounds Against *M. bovis, M. tuberculosis* (Sensitive and Multi-drug Resistant) and *Clostridium difficile*

In Vitro Inhibition of *Clostridium difficile*

Minimum inhibitory concentration (MIC; µg/mL) of test drugs against *Clostridium difficile* ATCC 17857 was determined by broth microdilution method using inoculum, media, incubation conditions and end-point in accordance with approved standards of the National Committee for Clinical Laboratory Standards (NCCLS, National Committee for Clinical Laboratory Standards. 1993. Methods for antimicrobial susceptibility testing of anaerobic bacteria. M11-A3. Third edition. National Committee for Clinical Laboratory Standards, Villanova, Pa.) except for the following modification: Oxyrase® enzyme (Oxyrase Inc., Mansfield, Ohio) was incorporated in Wilkins-Chalgren broth (Remel, Lenexa, Kans.) to produce anaerobic conditions and preclude any requirement for anaerobic atmosphere incubation (Spangler, S. K. et al. "Oxyrase, a method which avoids $CO_2$ in the incubation atmosphere for anaerobic susceptibility testing of antibiotics affected by $CO_2$," *J. Clin. Microbial.* 31:460–462 (1993); Spangler, S. K. et al., "Susceptibilities of 201 anaerobes to erythromycin, azithromycin, clarithromycin, and roxithromycin by Oxyrase agar dilution and E-test methodologies," *J. Clin. Microbial.* 33:1366–1367 (1995)). Thus, the use of this method allowed incubation in ambient air rather than the $CO_2$, $H_2$ and $N_2$- enriched atmosphere normally present in anaerobic chambers and jars. The Oxyrase both dilution method precluded the need of such equipment and provided a mechanism of avoiding the effects of $CO_2$ on the pH of the medium and in turn on the activity of test compounds. Falsely elevated MICs due to $CO_2$-dependent decrease in the pH has been previously demonstrated (Barry, A. L. et al., "In-vitro potency of azithromycin against gram-negative bacilli is method-dependent," *J. Antimicrob. Chernother.* 28:607–610 (1991), Hansen, S. L. et al., "Effect of carbon dioxide and pH on susceptibility of *Bacteroides fragilis* group to erythromycin," *Antimicrob. Agents Chernother.* 19:335–336 (1981), Ketsema, J. A. et al., "Significance of environmental factors on the in vitro potency of azithromycin," *Eur. J. Clin. Microbiol. Infect. Dis.* 10:834–842 (1991)). This problem is eliminated by using Oxyrase, since this enzyme removed $O_2$ rapidly converting it to $H_2O$ without toxic intermediates. Quality control anaerobic microorganisms (*Bacteroides thetaiotamicrons* ATCC 29741; *Eubacterium lentum* ATCC 43055) were tested in Oxyrase broth microdilution against clindamycin, metronidazole, mezlocillin, and vancomycin for quality assurance. Results were accepted when MICs of these recommended strains were within the acceptable ranges published by the NCCLS (National Committee for Clinical Laboratory Standards, *Methods for antimicrobial susceptibility testing of anaerobic bacteria.* M11-A3. Third edition. National Committee for Clinical Laboratory Standards, Villanova, Pa., 1993).

In Vitro Inhibition using (rBCG) LUX Method

Stock solutions of test compounds were prepared in dimethyl sulfoxide (DMSO; Sigma). These stocks were further diluted in DMSO to obtain concentrations suitable for minimum inhibitory concentration (MIC) or screening determinations. For MIC tests, two-fold dilutions ranging from 8.0 μg/mL to 0.06 μg/mL were used. For screening purposes, four concentrations were tested: 25.0, 5.0, 1.0 and 0.2 μg/mL.

A recombinant strain of *Mycobacterium bovis* bacille Calmette Guerin (rBCG) was employed as the challenge organism. This strain was transformed with an integrative shuttle vector carrying a firefly luciferase (lux) expression cassette. This vector was designated pMV361-lux.

A logarithmic phase culture of the rBCG:pMV361-lux strain was prepared in Middlebrook 7H9 broth (Difco) supplemented with 10% (v/v) ADC enrichment (BBL) and 0.5% (v/v) glycerol. The culture was diluted to obtain a final bacterial inoculum of 1×105 colony forming units per mL. A 2 mL culture volume was inoculated with 50 μL of each concentration of test compound. Control tubes containing rBCG:pMV361-lux in the absence of antibiotic were included. Isoniazid (Sigma) was included as a control in each assay run. Assay tubes were incubated at 37° C. for six days.

Luciferase activity was assessed by assay of 0.1 mL aliquots from each tube in an opaque white 96-well microtiter plate. Reactions were initiated by automated injection of 0.1 mL luciferin (1 mM) in a Wallac Autolumat model 96P luminometer. The MIC or lowest active concentration value was defined as the lowest concentration of compound which yielded a luminescence reading <1/100 the value obtained for the antibiotic-free growth control.

Minimum Inhibitory Concentration (MIC) as Determined by the BACTEC® Method

The BACTEC® system, available from Becton-Dickenson Diagnostic Instrument Systems, Sparks, MD, uses a radiorespirometric principle whereby carbon dioxide released by catabolism of $^{14}$C-labeled palmitic acid is spectrophotometrically detected and quantitated in arbitrary units of measurement referred to as Growth Index (GI) units. Endpoint determination criteria for BACTEC protocols are based on a conventional one per cent resistance cut-off, wherein the organism under scrutiny is deemed resistant to the concentration of drug being tested if growth of greater than one per cent of the bacterial population is observed. Thus, a comparison is made between growth in the presence of the antimicrobial agent and growth of the same Organism diluted $10^2$ in drug-free medium. BACTEC vials are inoculated with 0.1 mL of the organism (final bacterial concentration, 1–5×$10^5$ colony forming units per mL) and 0.1 mL of various concentrations of the antimicrobial agent. GI values are monitored daily until a value of>30 is achieved for the $10^{-2}$ control. The change in GI values (GI) is then used to determine susceptibility of the organism to each agent concentration tested. If the GI of the control is greater than that of the drug, then the organism is considered susceptible to that concentration. Conversely, if the GI of the control has a lower value than that of the drug, this indicates resistance. The drug is considered to have borderline activity at a particular concentration if the GI value of the control and drug are equal.

Minimum Inhibitory Concentrations (MICs)

The minimum inhibitory concentrations (MIC) of various 3(S)-alkoxy-6-nitro-2H-3,4-dihydro-[2-1b]imidazopyran antibacterial compounds against *M. bovis* BCG (recombinant strain, using LUX method described above), *M. tuberculosis* (H37Rv sensitive strain and multidrug-resistant, both using the BACTEC method) and *Clostridium difficile* were determined for compounds synthesized using the procedures described herein having the general structure:

where R is the substituent shown in Table 1. The results are shown in Table 1.

TABLE 1

Minimum Inhibitory Concentrations (MIC) of 3(S)-Alkoxy-6-nitro-2H-3,4-dihydro-[2-1b]imidazopyran Antibacterial Compounds Against *M. bovis, M. tuberculosis* (Sensitive and Multidrug-Resistant) and *Clostridium difficile*

| | | MIC (mg/mL) | | | |
|---|---|---|---|---|---|
| PA No. | R | A[a] | B[b] | C[b] | D |
| 602 | $CH_2(CH_2)_6CH_3$ | <5.0 | — | — | 3.12 |
| 626 | geranyl | 0.5 | 0.13 | — | 0.8 |
| 636 | $4\text{-}CF_3C_6H_4CH_2$ | 0.5 | — | — | 3.12 |
| 646 | $2,4\text{-}diCF_3C_6H_3CH_2$ | <5.0 | — | — | 3.12 |
| 647 | $4\text{-}PhCH_2OC_6H_4CH_2$ | 0.03 | 0.03 | ≦0.015 | 12.50 |
| 651 | $C_6H_5CH_2$ | >5.0 | — | — | 3.12 |
| 652 | $C_6F_5CH_2$ | >5.0 | — | — | 3.12 |
| 653 | $4\text{-}t\text{-}butylC_6H_4CH_2$ | 0.06 | 0.03 | ≦0.015 | 3.12 |
| 654 | $2,4\text{-}diFC_6H_3CH_2$ | >5.0 | — | — | 3.12 |
| 655 | $4\text{-}FC_6H_4CH_2$ | >5.0 | — | — | 6.25 |
| 736 | $4\text{-}CH_3OC_6H_4CH_2$ | 8.0 | — | — | — |
| 820 | $3\text{-}PhCH_2OC_6H_4CH_2$ | <5.0 | — | — | 3.12 |
| 822 | $4\text{-}n\text{-}butylC_6H_4CH_2$ | 0.06 | — | — | 12.5 |
| 824 | $4\text{-}CF_3OC_6H_4CH_2$ | 0.06 | — | — | — |

[a]LUX method
[b]BACTEC method
A = *Mycobacterium bovis* BCG (recombinant strain), LUX method
B = *Mycobacterium tuberculosis* H37Rv (sensitive strain), BACTEC method
C = *Mycobacterium tuberculosis* (multidrug-resistant strain), BACTEC method
D = *Clostridium difficile* ATCC 17857

EXAMPLE 26

Minium Inhibitory Concentrations (MIC) of 3(R)-Alkoxy-6-nitro-2H-3,4-dihydro-[2-1b]imidazopyran Antibacterial Compounds Against *M. bovis, M. tuberculosis* (Sensitive and Multidrug-Resistant) and *Clostridium difficile*

The procedures of Example 25 were followed to determine the minimum inhibitory concentrations of various 3(K)-alkoxy-6-nitro-2H-3,4-dihydro-[2-1b]imidazopyran antibacterial compounds prepared using the procedures described herein, having the following general formula:

where R is the substituent shown in Table 2. The results are shown in Table 2.

TABLE 2

Minimum Inhibitory Concentrations (MIC) of 3(R)-Alkoxy-6-nitro-2H-3,4-dihydro-[2-1b]imidazopyran Antibacterial Compounds Against *M. bovis, M. tuberculosis* (Sensitive and Multi-drug Resistant) and *Clostridium difficile*

| | | MIC (mg/mL) | | | |
|---|---|---|---|---|---|
| PA No. | R | A[a] | B[b] | C[b] | D |
| 601 | $CH_2(CH_2)_6CH_3$ | 8.0 | — | — | 1.50 |
| 684 | geranyl | >5.0 | — | — | 6.25 |
| 685 | $4\text{-}CF_3C_6H_4CH_2$ | >5.0 | — | — | 12.50 |
| 686 | $2,4\text{-}diCF_3C_6H_3CH_2$ | >5.0 | — | — | 3.12 |
| 687 | $4\text{-}PhCH_2OC_6H_4CH_2$ | >5.0 | — | — | 6.25 |
| 692 | $C_6H_5CH_2$ | >5.0 | — | — | 6.25 |
| 693 | $C_6F_5CH_2$ | >5.0 | — | — | 6.25 |
| 694 | $4\text{-}t\text{-}butylC_6H_4CH_2$ | >5.0 | — | — | 1.5 |
| 695 | $2,4\text{-}diFC_6H_3CH_2$ | >5.0 | — | — | 6.25 |
| 696 | $4\text{-}FC_6H_4CH_2$ | >5.0 | — | — | 6.25 |

[a]LUX method
[b]BACTEC method
A = *Mycobacterium bovis* BCG (recombinant strain), LUX method
B = *Mycobacterium tuberculosis* H37Rv (sensitive strain), BACTEC method
C = *Mycobacterium tuberculosis* (multidrug-resistant strain), BACTEC method
D = *Clostridium difficile* ATCC 17857

EXAMPLE 27

In Vivo Inhibition of *Mycobacterium bovis* (rBCG)

A recombinant strain of *Mycobacterium bovis* bacille Calmette Guerin (rBCG) was employed as the challenge organism. This strain had been transformed with an extra-chromosomal shuttle vector carrying a firefly luciferase (lux) expression cassette. This vector was designated pMH30. Female BALB/c mice aged 4 to 6 weeks were used. Five animals were included in each test group. One group was included which did not receive any drug therapy. A logarithmic phase culture of the rBCG:pMH30 strain was prepared in Middlebrook 7H9 broth (Difco) supplemented with 10% (v/v) ADC enrichment (BBL), 0.5% (v/v) glycerol and 20 µg/mL kanamycin.

A 150 µL volume of culture containing approximately $1 \times 10^7$ colony forming units per mi was injected into the tail vein of each mouse. Drug therapy was initiated 24 hours after infection. Compounds PA-647 and PA-653 (see Example 25) were administered daily by oral gayage (50 mg/kg). Animals were sacrificed by cervical dislocation ten days after initiation of therapy. Spleens were removed from each animal and homogenized in sterile Dulbecco's PBS (Gibco) containing 1% Triton X100. Duplicate 200 pt, aliquots of the homogenate were assayed in a Wallac Autolumat model 953B luminometer. Mean RLU values, standard deviation from the mean and statistical significance (paired, two-tailed t-test) were calculated. The results are shown in the following Table 3:

TABLE 3

In vivo Antimycobacterial Activity of 3(S)-Alkoxy-6-nitro-2H-3,
4-dihydro-[2-1b]imidazopyran Antibacterial Compounds
Against *Mycobacterium bovis* (rBCG-lux

| Compound | Average RLUs | Std. Deviation | p Value[A] |
|---|---

-continued

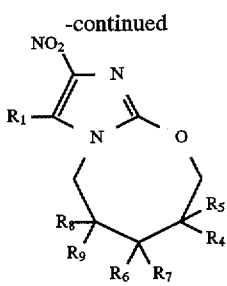

wherein R₆, R₇, R₈ and R₉ are independently selected from hydrogen, loweralkyl, alkylaryl, alkoxyalkyl, alkoxyalkylaryl, alkoxyalkylheterocycle, alkylarylalkylaryl, alkylarylaryl, alkylcycloalkyl, alkoxyaryl, alkylheterocycle, and alkoxyheterocycle; and the pharmaceutically acceptable salts thereof.

7. The method of claim 6 wherein the bicyclic imidazole is a compound of the formula:

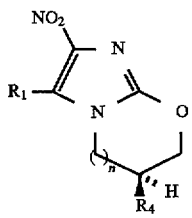

wherein $R_1$ is selected from the group consisting of hydrogen, halogen, loweralkyl, haloloweralkyl, cycloalkyl, heterocycle, substituted heterocycle and heterocyclicalkyl; $R_4$ and $R_5$ are independently selected from the group consisting of hydrogen, loweralkyl, aryl, alkylaryl, alkoxy, alkoxyalkyl, alkoxyalkylaryl, alkoxyalkylheterocycle, alkylarylalkylaryl, alkylarylaryl, alkylcycloalkyl, alkoxyaryl, carbamate, carboxamide, alkylheterocycle, and alkoxyheterocycle;. and n is 1, 2 or 3; and the pharmaceutically acceptable salts thereof.

8. The method of claim 6 wherein the pathogenic bacterium is selected from the group consisting of *Mycobacteria tuberculosis*, *Mycobacteria leprae*, and *Mycobacteria avium* complex.

9. The method of claim 8 wherein the pathogenic mycobacterium is *Mycobacteria tuberculosis*.

10. The method of claim 9 wherein the pathogenic mycobacterium is a multidrug-resistant strain of *Mycobacteria tuberculosis*.

11. The method of claim 5 wherein the pathogenic bacterium is *Clostridium difficile*.

12. A method of treating a human or animal subject suffering from an infection by pathogenic mycobacteria or clostridium comprising administering to the subject a therapeutically effective amount of a bicyclic nitroimidazole compound of the formula:

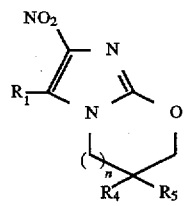

wherein $R_1$ is hydrogen, halogen, loweralkyl, haloloweralkyl, cycloalkyl, heterocycle, substituted heterocycle and heterocyclicalkyl; and $R_4$ and $R_5$ are independently selected from hydrogen, loweralkyl, aryl, alkylaryl, alkoxy, alkoxyalkyl, alkoxyalkyl, alkoxyalkoxyaryl, carbamate, carboxamide, alkylheterocycle, and alkoxyheterocycle; and n is 1, 2 or 3;

provided that when n is 2 or 3, the compounds of formula II can be additionally substituted as follows:

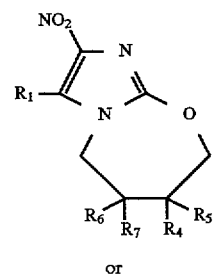

or

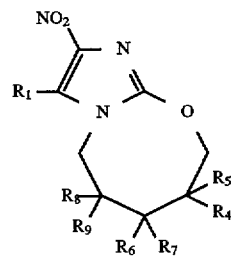

wherein R₆, R₇, R₈ and R₉ are independently selected from hydrogen, loweralkyl, aryl, alkylaryl, alkoxyalkyl, alkoxyalkylaryl, alkoxyalkylheterocycle, alkylarylalkylaryl, alkylarylaryl, alkylcycloalkyl, alkoxyaryl, alkylheterocycle, and alkoxyheterocycle; and the pharmaceutically acceptable salts thereof; alone or together with a pharmaceutically acceptable carrier.

13. The method of claim 12 wherein the human or animal subject is suffering from infection by pathogenic mycobacteria selected from the group consisting of *Mycobacteria tuberculosis*, *Mycobacteria leprae*, *Mycobacteria avium* complex and *Clostridium difficile*.

14. The method of claim 14 wherein the pathogenic bacterium is *Mycobacteria tuberculosis*.

15. The method of claim 13 wherein the pathogenic bacterium is a multidrug-resistant strain of *Mycobacteria tuberculosis*.

* * * * *

UNITED STATES PATENT AND TRADEMARK OFFICE
CERTIFICATE OF CORRECTION

PATENT NO. : 5,668,127
DATED : September 16, 1997
INVENTOR(S) : W.R. Baker et al.

It is certified that error appears in the above-identified patent and that said Letters Patent is hereby corrected as shown below:

| COLUMN | LINE | |
|---|---|---|
| [57] Pg. 1, col. 2 | Abstract 18 of text | "NK$_2$" should read --NR$_2$-- |
| [57] Pg. 1, col. 2 | Abstract formula IIa | "R$^6$" should read --R$_6$-- |
| [57] Pg. 1, col. 2 | Abstract formula IIa | "R$^7$" should read --R$_7$-- |
| [56] Pg. 2, col. 1 | Refs. Cited (Other Publs., Item 17) | "28: 607" should read --28:607-- |
| [56] Pg. 2, col. 1 | Refs. Cited (Other Publs., Item 18) | "19: 335" should read --19:335-- |
| [56] Pg. 2, col. 1 | Refs. Cited (Other Publs., Item 20) | "et at." should read --et al.-- |
| [56] Pg. 2, col. 2 | Refs. Cited (Other Publs., Item 28) | "et at." should read --et al.-- |

UNITED STATES PATENT AND TRADEMARK OFFICE
CERTIFICATE OF CORRECTION

PATENT NO. : 5,668,127
DATED : September 16, 1997
INVENTOR(S) : W.R. Baker et al.

It is certified that error appears in the above-identified patent and that said Letters Patent is hereby corrected as shown below:

| COLUMN | LINE | |
|---|---|---|
| [56] Pg. 2, col. 2 | Refs. Cited (Other Publs., Item 29) | "Oxide"," should read --Oxide,"-- |
| 2 | 51 | "dedvates" should read --derivates-- |
| 3 | 5 | "troirnidazole" should read --troimidazole-- |
| 3 | 5 | "Oxiranes,"*J.*" should read --Oxiranes," *J.*-- |
| 3 | 15 | after "et al" insert --.-- |
| 3 | 20 | "intimation" should read --inflammation-- |
| 3 | 42 | "DiseaseÒ" should read --Diseaseó-- |
| 6 | 11 | "roycebacteria" should read --mycobacteria-- |
| 6 | 12 | "in vive" should read --in vivo-- |
| 6 | 27 | "halloloweralkyl" should read --haloloweralkyl-- |
| 6 | 32 | "$R_4$and" should read --$R_4$ and-- |
| 7 | 65 | "saks" should read --salts-- |
| 8 | 19 | after "the like." start new paragraph |

UNITED STATES PATENT AND TRADEMARK OFFICE
CERTIFICATE OF CORRECTION

PATENT NO. : 5,668,127
DATED : September 16, 1997
INVENTOR(S) : W.R. Baker et al.

It is certified that error appears in the above-identified patent and that said Letters Patent is hereby corrected as shown below:

| COLUMN | LINE | |
|---|---|---|
| 8 | 47 | "group include" should read --groups include-- |
| 9 | 6 | "toweralkyl" should read --loweralkyl-- |
| 9 | 29 | "pyddazinyl" should read --pyridazinyl-- |
| 13 | 24 | "heterocycle )" should read --heterocycle)-- |
| 13 | 41 | "Keaction" should read --Reaction-- |
| 13 | 42 | "K-glycidol" should read --R-glycidol-- |
| 13 | 51 | "K=octyl" should read --R=octyl-- |
| 13 | 53 | "omefic" should read --omeric-- |
| 14 | 43 | "pierate" should read --picrate-- |
| 14 | 45 | "quatemized" should read --quaternized-- |
| 14 | 57 | "succmic" should read --succinic-- |
| 15 | 14 | "dally" should read --daily-- |
| 15 | 17 | "dally" should read --daily-- |
| 15 | 19 | "dallv" should read --dailv-- |

UNITED STATES PATENT AND TRADEMARK OFFICE
CERTIFICATE OF CORRECTION

PATENT NO. : 5,668,127
DATED : September 16, 1997
INVENTOR(S) : W.R. Baker et al.

It is certified that error appears in the above-identified patent and that said Letters Patent is hereby corrected as shown below:

| COLUMN | LINE | |
|---|---|---|
| 15 | 34 | "carders" should read --carriers-- |
| 15 | 53 | "adds" should read --acids-- |
| 16 | 18 | "multilameliar" should read --multilamellar-- |
| 16 | 25 | "oholines" should read --cholines-- |
| 16 | 35 | "Kepresentative" should read --Representative-- |
| 16 | 45 | "PDK" should read --PDR-- |
| 17 | 27 | "M+ff" should read --$(M+H)^+$--. |
| 17 | 48 | "$CH_2C_{12}$" should read --$CH_2Cl_2$--. |
| 17 | 61 | "$CHCl_3$" should read --$CHCl_3$-- |
| 18 | 54 | "Nail" should read --NaH-- |
| 18 | 66 | "cated" should read --calcd.-- |
| 18 | 66 | "$O_4$:C" should read --$O_4$: C-- |
| 18 | 66 | "H 7.80" should read --H, 7.80-- |
| 20 | 18 | "8.06" should read --$[\alpha]^{25}D$-- |

UNITED STATES PATENT AND TRADEMARK OFFICE
CERTIFICATE OF CORRECTION

PATENT NO. : 5,668,127
DATED : September 16, 1997
INVENTOR(S) : W.R. Baker et al.

Page 5 of 8

It is certified that error appears in the above-identified patent and that said Letters Patent is hereby corrected as shown below:

| COLUMN | LINE | |
|---|---|---|
| 20 | 20 | after "(d, 2H" insert --)-- |
| 20 | 21 | after "(s, 1H" insert --)-- |
| 20 | 23 | "MS 98" should read --MS 298-- |
| 20 | 30 | "dinitro imidazole" should read --dinitroimidazole-- |
| 20 | 50 | "NMP" should read --NMR-- |
| 20 | 55 | "0.44 ml" should read --0.44 mol-- |
| 20 | 67 | "1=4.2" should read --J=4.2-- |
| 21 | 7 | "N:" should read --$N_2$-- |
| 21 | 9 | after "NMR" delete the "." |
| 21 | 12 | "H)$^+$332" should read --H)$^+$ 332-- |
| 21 | 40 | "0.5M HC1" should read --0.5 M HCl-- |
| 21 | 52 | "imiidazopyrimidine" should read --imidazopyrimidine-- |
| 21 | 66 | "J$\subset$" should read --J=-- |

UNITED STATES PATENT AND TRADEMARK OFFICE
CERTIFICATE OF CORRECTION

PATENT NO. : 5,668,127
DATED : September 16, 1997
INVENTOR(S) : W.R. Baker et al.

It is certified that error appears in the above-identified patent and that said Letters Patent is hereby corrected as shown below:

| COLUMN | LINE | |
|---|---|---|
| 22 | 61 | before "min." insert --10-- |
| 23 | 52 | "octyl4" should read --octyl 4-- |
| 23 | 53 | "bromobutyramide" should read --bromo butyramide-- |
| 23 | 56 | "0.005N" should read --0.005 N-- |
| 23 | 61 | "octyl4" should read --octyl 4-- |
| 23 | 62 | "H MR" should read --H NMR-- |
| 23 | 63 | "(m, 2)" should read --(m, 2H)-- |
| 25 | 55 | "in ml" should read --in 5 ml-- |
| 25 | 65 | "CDCl$^3$" should read --CDCl$_3$-- |
| 25 | 67 | "NO$_2$:)" should read --NO$_2$)-- |
| 26 | 62 | "(p1.1" should read --(1.1-- |
| 28 | 22 | "of4" should read --of 4-- |
| 28 | 23 | "the4" should read --the 4-- |

UNITED STATES PATENT AND TRADEMARK OFFICE
CERTIFICATE OF CORRECTION

PATENT NO. : 5,668,127
DATED : September 16, 1997
INVENTOR(S) : W.R. Baker et al.

It is certified that error appears in the above-identified patent and that said Letters Patent is hereby corrected as shown below:

| COLUMN | LINE | |
|---|---|---|
| 28 | 47 | "with4" should read --with 4-- |
| 28 | 52 | after "Inhibitory" delete --.-- |
| 29 | 9 | "*Microbial.*" should read --*Microbiol.*-- |
| 29 | 13 | "*Microbial.*" should read --*Microbiol.*-- |
| 29 | 22 | "*Antirnicrob. Chernother.*" should read --*Antimicrob. Chemother.*-- |
| 29 | 25 | "*Chernother.*" should read --*Chemother.*-- |
| 29 | 26 | "Ketsema" should read --Retsema-- |
| 29 | 61 | "105" should read --$10^5$-- |
| 30 | 26 | "Organism" should read --organism-- |
| 30 | 27 | "$10^2$" should read --$10^{-2}$-- |
| 30 | 32 | "of>" should read --of >-- |
| 31 | 40 | "3(K)" should read --3(R)-- |
| 32 | 54 | "mi was" should read --ml was-- |
| 32 | 57 | "gayage" should read --gavage-- |
| 32 | 61 | "pt." should read --µL-- |
| 33 | 5 | after "lux" insert --)-- |
| 33 | 10 | after "229,079.91" delete --.-- |

UNITED STATES PATENT AND TRADEMARK OFFICE
CERTIFICATE OF CORRECTION

PATENT NO.    : 5,668,127
DATED         : September 16, 1997
INVENTOR(S)   : W.R. Baker et al.

It is certified that error appears in the above-identified patent and that said Letters Patent is hereby corrected as shown below:

| COLUMN | LINE | |
|---|---|---|
| 33 (Claim 1, | 29 line 15) | "$R_1$ and $R_5$" should read --$R_4$ and $R_5$-- |
| 35 (Claim 6, | 14 line 51) | after "loweralkyl," insert --aryl,-- |
| 36 (Claim 12, | 14 line 19) | replace the second occurrence "alkoxyalkyl" with --alkoxyaryl,-- |
| 36 (Claim 14, | 55 line 1) | "claim 14" should read --claim 13-- |

Signed and Sealed this

Fourteenth Day of September, 1999

Q. TODD DICKINSON

*Attest:*

*Attesting Officer*          *Acting Commissioner of Patents and Trademarks*